US008552066B2

(12) United States Patent
Rose et al.

(10) Patent No.: US 8,552,066 B2
(45) Date of Patent: *Oct. 8, 2013

(54) MODIFIED CHALCONE COMPOUNDS AS ANTIMITOTIC AGENTS

(75) Inventors: Seth D. Rose, Tempe, AZ (US); Rosemarie F. Hartman, Tempe, AZ (US)

(73) Assignee: Arizona Biomedical Research Commission, Phoenix, AZ (US)

( * ) Notice: Subject to any disclaimer, the term of this patent is extended or adjusted under 35 U.S.C. 154(b) by 215 days.

This patent is subject to a terminal disclaimer.

(21) Appl. No.: 12/777,212

(22) Filed: May 10, 2010

(65) Prior Publication Data

US 2010/0222380 A1   Sep. 2, 2010

Related U.S. Application Data

(63) Continuation of application No. 11/744,027, filed on May 3, 2007, now Pat. No. 7,714,025.

(60) Provisional application No. 60/799,014, filed on May 10, 2006.

(51) Int. Cl.
*A61K 31/16* (2006.01)
*C07D 233/70* (2006.01)
*C07D 319/00* (2006.01)

(52) U.S. Cl.
USPC ........ 514/629; 514/630; 514/676; 548/326.1; 568/327; 568/335

(58) Field of Classification Search
USPC ........ 548/326.1; 568/327, 335; 514/629, 630, 514/676
See application file for complete search history.

(56) References Cited

U.S. PATENT DOCUMENTS

| | | | |
|---|---|---|---|
| 3,666,756 | A | 5/1972 | Fukumura et al. |
| 4,605,674 | A | 8/1986 | Fujiu et al. |
| 5,110,927 | A | 5/1992 | Pitha et al. |
| 2004/0176471 | A1 | 9/2004 | Lin et al. |

FOREIGN PATENT DOCUMENTS

| | | |
|---|---|---|
| JP | S59-231531 | 6/1983 |
| JP | H05-061193 | 8/1991 |
| JP | H11-152475 | 11/1997 |
| JP | 2003527308 | 9/2003 |
| JP | 2003-528842 | 9/2008 |

OTHER PUBLICATIONS

Hasegawa R, Wang CY, Kim DJ, Lee MS, Yoshida Y, Ito N. Effect of acyl derivatives of 4,4,4-trifluoro-1-phenyl-1,3-butanedione on 2-acetylaminofluorene-induced glutathione S-transferase positive foci in the rat liver. Teratog., Carcinog. Mutagen. 1992;12;6, abstract.*

J. A. Hadfield, S. Ducki, N. Hirst, and A. T. McGown, Prog. Cell Cycle Res. 2003, 5, 309-325.
J. T. Huzil, R. F. Ludueña, and J. Tuszynski, Nanotechnol. 2006, 17, S90-S100.
L. Ni, C. Q. Meng, and J. A. Sikorski, Expert Opin. Ther. Patents 2004, 14(12), 1669-1691.
R. J. Anto, K. Sukumaran, G. Kuttan, M. N. A. Rao, V. Subbaraju, and R. Kuttan, Cancer Lett., 1995, 97, 33-37.
F. Herencia, M. L. Ferráandiz, A. Ubeda, J. N. Dominguez, J. E. Charris, G. M. Lobo, and M. J. Alcaraz, Bioorg. Med. Chem. Lett. 1998, 8, 1169-1174.
M. L. Edwards, D. M. Stemerick, and P. S. Sunkara, J. Med. Chem. 1990, 33(7), 1948-1954.
N.-H. Nam, Y. Kim, Y.-J. You, D.-H. Hong, H.-M. Kim, and B.-Z. Ahn, Eur. J. Med. Chem. 2003, 38, 179-187.
M. López-Lázaro, Curr. Med. Chem.—Anti-Cancer Agents 2002, 2, 691-714.
T. Akihisa, H. Tokuda, M. Ukiya, M. Iizuka, S. Schneider, K. Ogasawara, T. Mukainaka, K. Iwatsuki, T.Suzuki, and H. Nishino, Cancer Lett. 2003, 201, 133-137.
R. LeBlanc, J. Dickson, T. Brown, M. Stewart, H. N. Pati, D. VanDerveer, H. Arman, J. Harris, W. Pennington, H. L. Holt, Jr., and M. Lee, Bioorg. Med. Chem. 2005, 13, 6025-6034.
B. Shan, J. C. Medina, E. Santha, W. P. Frankmoelle, T.-C. Chou, R. M. Learned, M. R. Narbut, D. Stott, P. Wu, J. C. Jaen, T. Rosen, P. B. M. W. M. Timmermans, and H. Beckmann, Proc. Natl. Acad. Sci. USA 1999, 96, 5686-5691.
P. J. Britto, L. Knipling, and J. Wolff, J. Biol. Chem. 2002, 277(32), 29018-29027.
M. L. Go, X. Wu, and X. L. Lu, Curr. Med. Chem. 2005, 12, 483-499.
J. R. Dimmock, A. Jha, G. A. Zello, T. M. Allen, C. L. Santos, J. Balzarini, E. De Clercq, E. K. Manavathu, and J. P. Stables, Pharmazie 2003, 58(4), 227-232.
C. Combeau, J. Provost, F. Lancelin, Y. Tournoux, F. Prod'Homme, F. Herman, F. Lavelle, J. Leboul, and M. Vuilhorgne, Mol. Pharmacol. 2000, 57, 553-563.
R. F. Ludueña, and M. C. Roach, Pharmacol. Ther. 1991, 49, 133-152.
Goodman & Goldman's The Pharmacological Basis of Therapeutics, Ninth Edition (1996), Appendix II, pp. 1707-1711.
Goodman & Goldman's The Pharmacological Basis of Therapeutics, Tenth Edition (2001), Appendix II, pp. 475-493.
English et al., Principles of Organic Chemistry, 2nd Ed., McGraw-Hill Book Company, Inc. 245-7 (1956).

(Continued)

*Primary Examiner* — Andrew D Kosar
*Assistant Examiner* — Raymond Covington
(74) *Attorney, Agent, or Firm* — Banner & Witcoff, Ltd.

(57) ABSTRACT

Antimitotic agents comprising a modified chalcone or modified chalcone derivative are disclosed. The modified chalcone or modified chalcone derivative compounds are of the general formula CHAL-LIN-COV, wherein CHAL is a chalcone or chalcone derivative portion, LIN is an optional linker portion, and COV is a covalent bonding portion (e.g., an $\alpha,\beta$-unsaturated thiol ester group). The modified chalcone or modified chalcone derivative compounds provide an improved method of interference with tubulin polymerization, for example by covalent (and essentially irreversible) bonding between tubulin and the covalent bonding portion, potentially resulting in a decrease in tumor size and/or disappearance of the cancer, to the benefit of cancer patients.

18 Claims, No Drawings

(56) References Cited

OTHER PUBLICATIONS

Sinkula, A. A. and Yalkowsky, S. H.; Rationale for Design of Biologically Reversible Drug Derivatives: Prodrugs, Journal of Pharmaceutical Sciences, 64(2), 181-210 (1975).

S. Ducki, R. Forrest, J. A. Hadfield, A. Kendall, N. J. Lawrence, A. T. McGowan, and D. Rennison, Bioorg. Med. Chem. Lett., 1998, 8, 1051-1056.

International Search Report mailed Nov. 16, 2007, in counterpart PCT Patent Application No. PCT/US2007/011202.

S. Ducki et al. "Potent Antimitotic and Cell Growth Inhibitory Properties of Substituted Chalcones" Bioorganic & Medicinal Chemistry Letters vol. 8, No. 9 (1998) pp. 1051-1056.

F. Herencia et al. "Synthesis and Anti-Inflammatory Activity of Chalcone Derivatives" Bioorganic & Medicinal Chemistry Letters vol. 8, No. 10 (1998) pp. 1169-1174.

C.Q. Meng et al. "Discovery of Novel Heteroaryl-Substituted Chalcones as Inhibitors of TNF-Alpha-Induced VCAM-1 Expression" Bioorganic & Medicinal Chemistry Letters vol. 14, No. 6 (2004) pp. 1513-1517.

M. Edwards et al. "Chalcones: A New Class of Antimitotic Agents", Journal of Medicinal Chemistry, American Chemical Society, vol. 33, No. 7 (1990) pp. 1948-1954.

CA 134:127813 (2000).

CA 126:42241 (1996).

Laliberté et al. "Synthesis of New Chalcone Analogues and Derivatives"; Canadian journal of chemistry, 1968, vol. 46, p. 1952-1956.

Afanas'Eva, et al. "Dielectric Relaxation in Polymers and Copolyers of Methacrylates and Methacrylamides with Chromophoric Groups in Side Chains"; Physics of the Solid State, 2003, vol. 45, No. 5, p. 983-989.

Vasavada, et al. "Synthesis and Antimicrobial Screening of Cyclohexenones and Oxazines"; Journal of the Indian Chemical Society, 2003, vol. 80, No. 1, p. 55-56.

Zhongguo Yaowu Huaxue Zazhi, 2001, vol. 11, No. 4, p. 209-214.

Makita, et al. "Photo alignment Materials with High Sensitivity to Near UV Light", Journal of Photopolymer Science and Tehcnology, 1998, vol. 11, No. 2, p. 187-192.

Reddy, et al. "Synthesis, Characterization and Properties of novel Polymers Containing Pendant Photocrosslinkable Chalcone Moiety", European Polymer Journal, 1996, vol. 32, No. 8, p. 919-926.

Rejection Notice relating to corresponding JP Application No. 2009-509834, issued Sep. 19, 2012.

* cited by examiner

MODIFIED CHALCONE COMPOUNDS AS ANTIMITOTIC AGENTS

CROSS-REFERENCE TO RELATED APPLICATIONS

This application is a continuation of U.S. application Ser. No. 11/744,027, now allowed, which claims the benefit of priority of U.S. Provisional Patent Application No. 60/799,014, filed May 10, 2006. Each of these applications is hereby incorporated by reference in its entirety.

FIELD OF THE INVENTION

The present invention relates to antimitotic agents of the formula CHAL-LIN-COV, having a chalcone or chalcone derivative portion (CHAL) and a covalent bonding portion (COV) that is optionally bonded to CHAL through a linker portion (LIN). The covalent bonding portion may be an α,β-unsaturated thiol ester group. The modified chalcone or chalcone derivative compounds are designed to interfere with cell division processes in cancer cells, thereby reducing the unrestrained proliferation of cancer cells and/or decreasing tumor size, to the benefit of cancer patients.

BACKGROUND OF THE INVENTION

Cancer is characterized by invasive, unrestrained division of genetically aberrant cells. Such cells have lost many of the normal control mechanisms that regulate cell division, such as the requirement for external growth signals, contact growth inhibition, regulation by cell cycle checkpoints, and failure of cellular self-destruct mechanisms (apoptosis) triggered by abnormalities in the cell. Progressive genetic changes result in a cell that, for example, divides based on stimulation of mitogenic pathways in the cell independently of a growth signal from outside the cell, such as an external growth factor. Also, cells with genetic abnormalities would normally be arrested at various points in the cell cycle, whereupon biochemical processes would attempt to repair the damage, or if that were unsuccessful, to begin the orderly destruction of the cell through apoptosis. Cancer cells typically have lost the ability to proceed through apoptosis, leading to the survival of aberrant cells with invasive and proliferative characteristics.

Proliferation of cancer cells requires several functional biochemical processes. One is the ability to duplicate the DNA complement of the cell so that progeny cells will have a blueprint for growth and subsequent proliferation. This process involves the use of the endogenous cellular DNA as a template for the biochemical synthesis of a copy. As DNA is a double helix, this process produces two copies of the DNA, each in the form of a double helix. Each of the progeny cells receives one copy of the DNA.

The genetic material of human cells is not present as a single DNA molecule. Instead it is present as a group of DNA molecules. These molecules are not free-floating in the cellular milieu but rather are associated in a highly structured way with proteins in the nucleus of the cell. Such combination of DNA and nuclear proteins is referred to as chromatin. The partitioning of the chromatin into progeny cells proceeds by a highly organized process of the cell cycle known as mitosis.

Before mitosis, chromatin is in an uncondensed state, so that the genetic material is accessible as a blueprint for protein synthesis. During cell division, however, chromatin changes into a highly structured form consisting of condensed chromosomes. Because the DNA has already been duplicated prior to mitosis, two copies of each chromosome are present. They are attached to each other at a chromosomal feature known as the centromere. The two still-joined duplicate DNA-protein (condensed chromatin) assemblies are referred to as chromatids.

For the two progeny cells to succeed in obtaining one copy of each of the duplicated DNA molecules in the chromatids after mitosis, a proteinaceous fiber known as a spindle fiber (connected to each chromatid at the centromere) serves as a microscopic tether to pull the chromatids apart to opposite poles of the cell. This ultimately results in partitioning of the chromatids into the two progeny cells. The formation of spindle fibers is essential for the completion of mitosis and successful cell division. Consequently, the spindle fibers are one potential target in a strategy to obstruct cancer cell division. (J. A. Hadfield, S. Ducki, N. Hirst, and A. T. McGown, *Prog. Cell Cycle Res.* 2003, 5, 309-325)

The spindle fiber is composed of the protein tubulin. Tubulin exists in two similar forms, α and β tubulin. These two forms associate to form a dimer of tubulin composed of one molecule each of α and β tubulin, and the dimers then associate to form helical aggregates known as microtubules. The microtubule increases in length by polymerization of dimers of tubulin molecules at one end, whereas the microtubule shortens by loss of tubulin molecules at the other end. The polymerization and depolymerization of tubulin at the spindle fiber is essential for mitosis and the production of progeny cancer cells.

Additional roles of tubulin in cells include both the maintenance of cell shape and spatial organization of cell organelles. Failure of the former can lead to another possible anticancer action (in addition to inhibiting mitosis) of the anticancer agents based on interference with microtubule dynamics, namely the collapse of the microvasculature that provides the blood supply to the central regions of the tumor, precipitating dramatic necrosis of all but the peripheral regions of the tumor.

One class of anticancer agents in use therapeutically consists of tubulin polymerization/depolymerization inhibitors. Their mode of action is typically by interaction with tubulin molecules, resulting either in (1) a molecular complex that no longer has the ability to interact with other tubulin molecules required for polymerization of tubulin, or (2) stabilization of the tubulin molecules and preventing the depolymerization of the microtubule. Both modes of action render the spindle fiber unable to carry out its function in cell division. Anticancer compounds such as the vinca alkaloids prevent polymerization of tubulin, whereas anticancer taxanes prevent the depolymerization of tubulin. Both processes result in failure of mitosis. Cancer cells are typically more sensitive to such agents than normal cells are, and design of even more specific antimitotic agents may be based on different variants of tubulin (isotypes) present in cells. (J. T. Huzil, R. F. Ludueña, and J. Tuszynski, *Nanotechnol.* 2006, 17, S90-S100)

Chalcones are potent antimitotic agents of plant origin. (L. Ni, C. Q. Meng, and J. A. Sikorski, *Expert Opin. Ther. Patents* 2004, 14(12), 1669-1691; R. J. Anto, K. Sukumaran, G. Kuttan, M. N. A. Rao, V. Subbaraju, and R. Kuttan, *Cancer Lett.,* 1995, 97, 33-37) Synthetic ones designed for anticancer testing are structurally similar to antimitotic agents such as colchicine and Combretastatin A-4, as shown below:

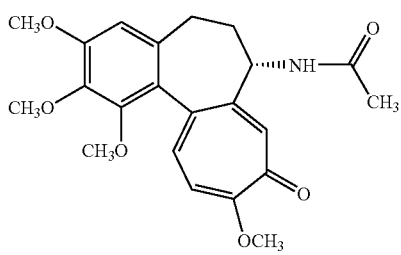

Colchicine

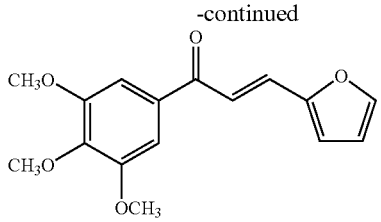

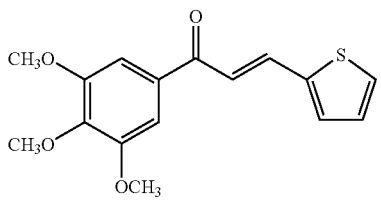

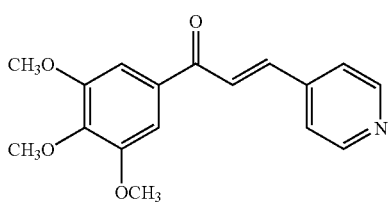

Combretastatin A-4

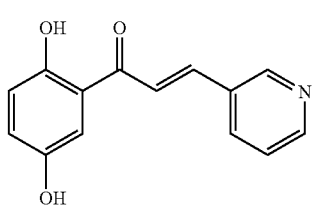

A synthetic chalcone

The synthetic chalcone shown above with colchicine and Combretastatin A-4 is designed particularly to associate non-covalently with tubulin. The pattern of ring substitution with OCH$_3$ and OH groups is thought to be important in this association with tubulin, and the CH$_3$ group on the enone C=C is believed to confer stability on the s-trans conformation (i.e., trans at the single bond between O=C and C=C), as is shown. The s-trans conformation is thought to have enhanced ability to associate with tubulin.

Chalcones may also bear heterocyclic groups, as in the case of the three furans, thiophene, two pyridines, indole, and two quinoline groups shown below (F. Herencia, M. L. Ferrándiz, A. Ubeda, J. N. Dominguez, J. E. Charris, G. M. Lobo, and M. J. Alcaraz, *Bioorg. Med. Chem. Lett.* 1998, 8, 1169-1174; M. L. Edwards, D. M. Stemerick, and P. S. Sunkara, *J. Med. Chem.* 1990, 33(7), 1948-1954; N.-H. Nam, Y. Kim, Y.-J. You, D.-H. Hong, H.-M. Kim, and B.-Z. Ahn, *Eur. J. Med. Chem.* 2003, 38, 179-187):

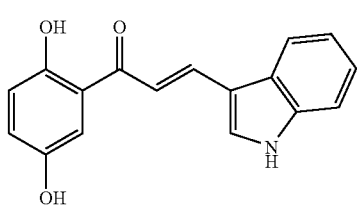

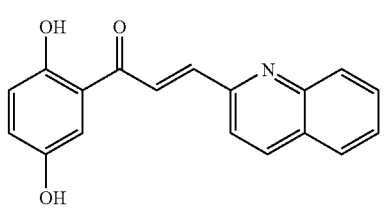

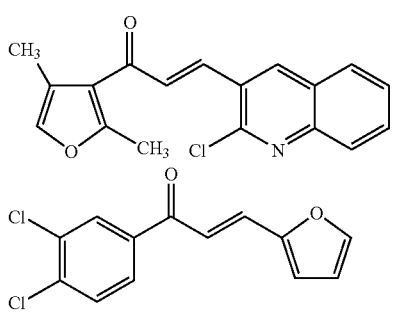

Derivatives of chalcones include structures such as their corresponding flavones, where the C=C—C=O of the parent chalcone (from which the structure is derived) becomes part of a fused ring system. Saturation of the C=C yields the corresponding flavanone derivative of a chalcone. (M. López-Lázaro, *Curr. Med. Chem.—Anti-Cancer Agents* 2002, 2, 691-714; T. Akihisa, H. Tokuda, M. Ukiya, M. Iizuka, S. Schneider, K. Ogasawara, T. Mukainaka, K. Iwatsuki, T. Suzuki, and H. Nishino, *Cancer Lett.* 2003, 201, 133-137) and pyrazoles (R. LeBlanc, J. Dickson, T. Brown, M. Stewart, H. N. Pati, D. VanDerveer, H. Arman, J. Harris, W. Pennington, H. L. Holt, Jr., and M. Lee, *Bioorg. Med. Chem.* 2005, 13, 6025-6034), examples of which are shown below:

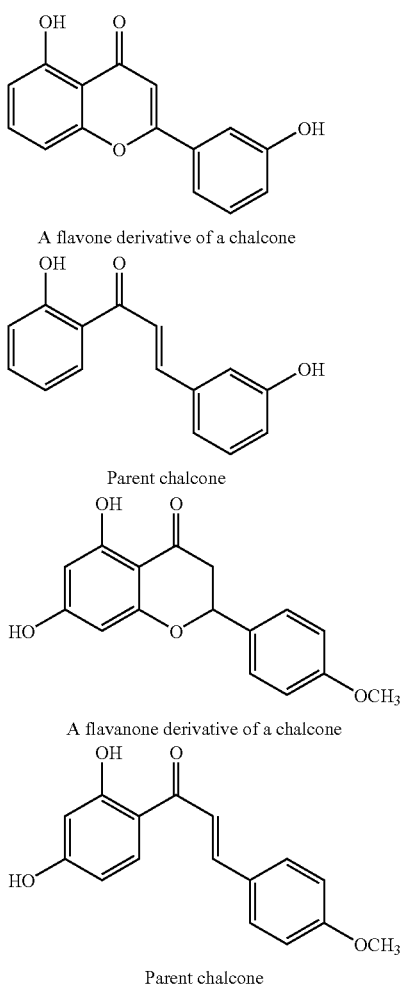

A flavone derivative of a chalcone

Parent chalcone

A flavanone derivative of a chalcone

Parent chalcone

There are several disadvantages inherent in conventional antimitotic inhibitors of tubulin polymerization and/or depolymerization. One is reversibility of binding of the antimitotic agent to tubulin and/or microtubules. Others include the development of drug resistance by the tumor, toxicity to the patient, and limited solubility/bioavailability through oral, parenteral, or other routes of administration to the patient. Development of drug resistance by a tumor results in resumption of growth of the tumor and increase in tumor size and tumor burden on the patient, often with fatal results. Toxicity to the patient results in limitations on the dose that can safely be administered (maximum tolerated dose, MTD), thus limiting the achievable antitumor effect of the compound. Limited solubility of the antimitotic agent limits the concentration of the agent that can be delivered to the tumor through typical means of administration (e.g., dissolved in the bloodstream).

SUMMARY OF THE INVENTION

To address the current limitations of cancer therapies based on tubulin polymerization inhibition, Applicants disclose several features and combinations of features which lead to improvements in the design of antimitotic chalcones. These improvements are based on modifications of chalcones or chalcone derivatives, such that a single molecule includes (1) the antimitotic and antitumor characteristics of a chalcone, and (2) the ability to readily form a covalent bond to the tubulin molecule or another cellular biomolecule essential to mitosis.

The combined molecule (or modified chalcone or modified chalcone derivative) has a substructure comprising a chalcone or chalcone derivative. This imparts antimitotic and antitumor characteristics to the molecule. A preferred embodiment of this invention may also contain a chemical linker portion having a group of bonded atoms between the chalcone or chalcone derivative portion of the molecule and the covalent bonding portion of the molecule. The functions of this linker are to allow the chalcone-like portion of the molecule to optimally interact with binding sites for chalcones on tubulin or another biomolecule important in cell division and/or to allow the covalently reactive portion of the molecule to optimally interact with reactive chemical groups that are part of the tubulin molecule or another biomolecule important in cell division.

The advantages of covalent binding of the antimitotic agent to its biomolecular target are severalfold. First, drug resistance developed by cancer cells often results from the cells' enhanced ability to expel the drug from the cell, typically by a protein known as the P-glycoprotein pump. Unfortunately, exposure to one drug can result in an activation of the P-glycoprotein pump, with the result that broad classes of antitumor drugs are expelled and are no longer useful for treatment, a phenomenon known as multidrug resistance (MDR).

Antimitotic agents that reversibly bind to their targets may be thought of as existing in two states: free in the cytoplasm and bound to their biomolecular target(s). A quasi-equilibrium defines the ratio of the concentration of the drug in these two states. Once expulsion of the drug is underway, maintenance of this quasi-equilibrium requires release of the drug from the bound state(s). This process can free the biomolecular target from the destructive effect of the antimitotic agent, rendering the drug ineffectual or mitigating the benefit of treatment. Compounds disclosed herein are capable of forming covalent bonds to the biomolecular target (e.g., tubulin). The consequence of covalent bonding of the drug to the target is that the bound state is essentially irreversibly formed. In other words, the action of the P-glycoprotein pump is limited to removal of unbound drug from the cytoplasm, as the covalently bonded drug-target adduct does not readily come apart. Because of the formation of a covalent bond, there is not a reversible, quasi-equilibrium governing the binding of the agent to the target.

The covalently reactive group incorporated into the inventive antimitotic agents is selected on the basis of the unique requirements of the use of the antimitotic agent. For example, target biomolecules such as tubulin bear amino acid side chains with highly nucleophilic groups (e.g., the sulfhydryl group (—SH) of cysteine (also known as a thiol group)). In particular, the sulfhydryl group of cysteine residue number 239 in β-tubulin is reactive as a nucleophile and readily reacts with electrophilic groups in other molecules. (B. Shan, J. C. Medina, E. Santha, W. P. Frankmoelle, T.-C. Chou, R. M. Learned, M. R. Narbut, D. Stott, P. Wu, J. C. Jaen, T. Rosen, P. B. M. W. M. Timmermans, and H. Beckmann, *Proc. Natl. Acad. Sci. USA* 1999, 96, 5686-5691; D. Clark, W. Frankmoelle, J. Houze, J. C. Jaen, and J. C. Medina, U.S. Pat. No. 6,433,187) It is understood that actually the more reactive form of the thiol (R—S—H) is the deprotonated form, i.e., the thiolate (R—S$^-$). Indeed, cysteine residues in active sites of enzymes often have lower $pK_a$ values than cysteine residues located elsewhere in an enzyme, so active-site cysteine residues often experience a greater degree of ionization to the thiolate form at physiological pH values, rendering such cysteine residues more nucleophilic than ordinary cysteine residues in proteins. Furthermore, as in the case of cysteine residues in tubulin, the electrostatic environment of the cysteine residue can enhance the ability to ionize and thereby be converted into the more reactive thiolate form. (P. J. Britto, L. Knipling, and J. Wolff, *J. Biol. Chem.* 2002, 277(32), 29018-29027) Hence, for reaction with tubulin cysteine nucleophiles, cysteine nucleophiles in enzymes involved in mitosis, and other nucleophilic groups in biomolecules involved in mitosis, an electrophilic group may be beneficially incorporated into the antimitotic agents.

Reactions of electrophiles and nucleophiles by nucleophilic substitution results in the substitution of the nucleophile for a leaving group in the electrophile. Thus, the liberated leaving group is a byproduct of the substitution reaction. This may not be desirable due to possible harmful effects of the liberated leaving group. To avoid the release of a potentially harmful leaving group, it is possible to incorporate an electrophilic group that does not undergo nucleophilic substitution but rather nucleophilic addition. In nucleophilic addition, all the atoms of the nucleophile and of the electrophile become incorporated into the addition product or adduct resulting from bonding of the nucleophile and electrophile. Thus, the electrophilic group can react with the nucleophilic group without production of harmful byproducts. In one class of electrophiles, there is a carbon-carbon double bond in conjugation with a carbon-oxygen double bond (i.e., C=C—C=O). The C=O polarizes the C=C that it is conjugated to, thereby making the C=C a positively charged site of reactivity for nucleophiles. Upon treatment with a nucleophile (Nu⁻H⁺), the electrophile undergoes reaction at the C=C to produce the addition product:

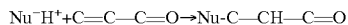

Not all molecules bearing the C=C—C=O conjugated system, however, will readily undergo nucleophilic addition according to the above mechanism. For example, the C=C—C=O system of the chalcone itself is not thought to be sufficiently reactive to readily couple to a cysteine of tubulin. (M. L. Go, X. Wu, and X. L. Lu, *Curr. Med. Chem.* 2005, 12, 483-499) Some C=C—C=O systems thought to be electrophilic have been reported to exhibit cytotoxicity. (J. R. Dimmock, A. Jha, G. A. Zello, T. M. Allen, C. L. Santos, J. Balzarini, E. De Clercq, E. K. Manavathu, and J. P. Stables, *Pharmazie* 2003, 58(4), 227-232) Other C=C—C=O systems, for example those having the structures below, are likewise thought to exhibit electrophilic behavior. (C. Combeau, J. Provost, F. Lancelin, Y. Tournoux, F. Prod'Homme, F. Herman, F. Lavelle, J. Leboul, and M. Vuilhorgne, *Mol. Pharmacol.* 2000, 57, 553-563; R. F. Luduena, and M. C. Roach, *Pharmacol. Ther.* 1991, 49, 133-152):

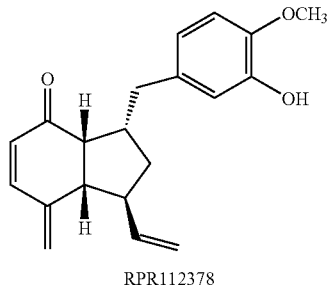

RPR112378

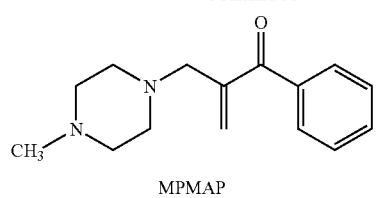

MPMAP

The above structures, however, share the disadvantageous feature of having the α,β-unsaturated ketone substructure embedded as an inherent part of the molecular system. Modification of the location and/or reactivity of this substructure is therefore difficult if not impossible to achieve.

Besides ease of synthesis of molecules of varying reactivity and specificity, a further aspect of the system of atoms C=C—C=O in the antimitotic agents of the present invention is a proper balance of reactivity and stability. Sufficient stability is required for the agent to reach its target of tubulin or other biomolecule important in mitosis and to be sufficiently reactive once there. One possible C=C—C=O system, for example, is an α,β-unsaturated thiol ester group:

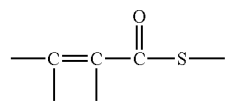

An advantage of the above α,β-unsaturated thiol ester group as an electrophile for reaction with the nucleophilic thiol group of, for example, cysteine-239 of β-tubulin is that it can readily be attached to chalcone derivatives at varying positions of the molecule, to optimize reactivity and specificity. Also, simple variations in the nature of the substituents on the C=C can optimize reactivity of the electrophilic system.

In view of the above, the present invention in one embodiment is an antimitotic agent having the general Formula I:

CHAL-LIN-COV (I)

or a pharmaceutically acceptable salt, ester, or prodrug thereof, wherein CHAL is a chalcone or chalcone derivative portion, LIN is an optional linker portion, and COV is a covalent bonding portion, wherein CHAL, LIN, and COV are as defined herein.

Particular embodiments of the invention include compounds represented by the Formulas 1a', 1b', 1c', and 1d':

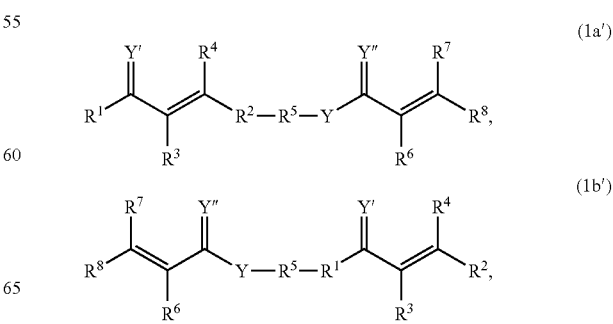

-continued

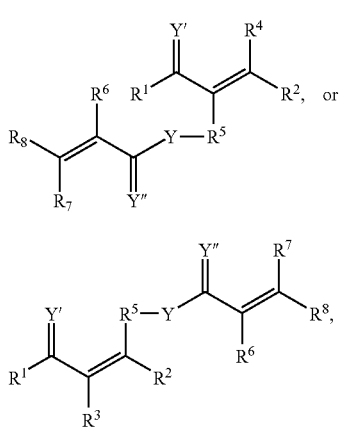

(1c')

(1d')

or a pharmaceutically acceptable salt, prodrug, or ester thereof, wherein $R^1$-$R^4$, $R^6$-$R^8$, Y, Y', and Y" are as defined herein. A preferred embodiment of the invention is directed to compounds having the Formula 1a' above. In another embodiment, the invention is directed to compounds having the Formula 1b' above, with the proviso that the compound is not a compound of the formula

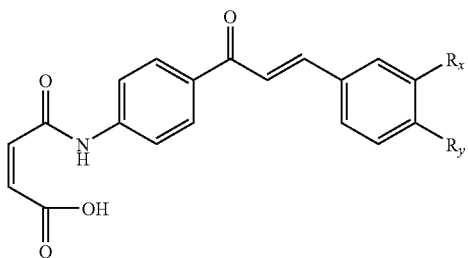

wherein $R_x$ and $R_y$ are independently selected from the group consisting of hydrogen, methyl, methoxy, —Cl, and —$NO_2$. Other embodiments of the invention include compounds having the formulas 1c' or 1d', respectively.

In compounds represented by any of the above Formulas 1a', 1b', 1c', and 1d', $R^5$ represents a bond or optionally a linker portion, as described herein, between CHAL and COV in Formula I above. In a preferred embodiment, as shown in Formula 1a', $R^5$ and/or the covalent bonding portion (COV) may be bonded to $R^2$ of the chalcone or chalcone derivative portion (CHAL), where $R^2$ is in a trans relationship with the C=Y' group. In another embodiment, as shown in Formula 1d', $R^5$ and/or the covalent bonding portion (COV) may be bonded in a cis relationship with the C=Y' group. In still other embodiments, as shown in Formulas 1b' and 1c', $R^5$ and/or the covalent bonding portion (COV) may be bonded to other points of the chalcone or chalcone derivative portion (CHAL). Particular embodiments include the above compounds of Formulas 1a', 1b', 1c', or 1d', wherein Y is —S—, and Y' and Y" are both =O.

In another embodiment, the present invention is a pharmaceutical composition comprising one or more of the above antimitotic agents and one or more pharmaceutically acceptable carriers. Such pharmaceutical compositions may be used, for example, in preventing or inhibiting the growth of a cancer cell in a patient, by administering to the patient a therapeutically effective amount of the pharmaceutical composition. Pharmaceutical compositions are effective in the treatment or prevention of a number of types of cancers including pancreatic, colon, colorectal, lung, prostate, breast, and urinary bladder cancer. Other types of cancers such as leukemia and fibrosarcoma may also be treated. Patients who may be treated include mammals (both human and animal patients).

In another embodiment, the present invention is a method for the treatment or prevention of cancer in a patient. The method comprises administering to the patient a therapeutically effective amount of a pharmaceutical composition described above.

In another embodiment, the present invention is a method of inhibiting the growth of a cancer cell in vitro. The method comprises contacting the cancer cell with an antimitotic compound, as described herein. Preferably, the compound is highly effective, such that 50% growth inhibition of the cancer cell is achieved with a concentration of the compound ($GI_{50}$) of less than about 50 micromolar.

DETAILED DESCRIPTION OF THE INVENTION

As indicated above, many factors in terms of both chemical and biological functionality are significant in the development of antimitotic agents having a high degree of effectiveness. In this regard, Applicants have discovered a class of compounds having a chalcone or chalcone derivative portion that is modified with a covalent bonding portion. Importantly, the latter portion can covalently bond to tubulin or other cellular mitotic agent through a number of reaction pathways, including electrophilic addition to nucleophilic groups (e.g., sulfhydryl) present in the target biomolecule. Covalent bonding results in irreversible inactivation of mitotic biomolecules, while the addition mechanism (rather than substitution) eliminates the generation of potentially harmful leaving groups.

Advantageously, the covalent bonding portion is sufficiently stable to reach intracellular targets in effective amounts (i.e., without degrading to an extent such that its effectiveness in causing a desired biochemical and/or therapeutic effect is appreciably compromised). The covalent bonding portion is also sufficiently reactive to attenuate or inhibit the normal function of the targets. The covalent bonding portion itself may vary in terms of the nature of the substituents about its core structure. It may also vary in terms of its positioning (with respect to both location and distance) relative to the chalcone or chalcone derivative portion, by virtue of attachment at a number of possible sites and optionally through the use of a linker portion.

In one embodiment, the present invention is an antimitotic agent having the general Formula I:

CHAL-LIN-COV    (I)

wherein CHAL is a chalcone or chalcone derivative portion, LIN is an optional linker portion, and COV is a covalent bonding portion.

Chalcone or Chalcone Derivative Portion (CHAL)

In various embodiments of the invention, the group represented by CHAL has the Formula (1a):

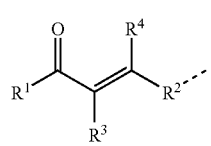

(1a)

with the dashed line indicating the point of attachment or bonding between CHAL- and -COV, optionally occurring through the linker portion -LIN-, as shown above in Formula I.

In other embodiments, this point of attachment or bonding occurs at other locations of the chalcone or chalcone derivative portion of the molecule, wherein CHAL is represented by Formulas (1b), (1c), and (1d) below:

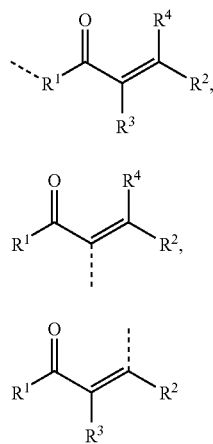

The chalcone or chalcone derivative portion CHAL is characterized by cyclic (e.g., monocyclic, bicyclic, or tricyclic) groups at the $R^1$ and $R^2$ positions. $R^1$ and $R^2$ therefore represent cyclic radicals independently selected from cycloalkyl, heterocycloalkyl, aryl, or heteroaryl which may optionally be independently substituted at one or more substitutable ring positions with the same radicals as defined for $R^3$ or $R^4$ below. Additionally or otherwise, the cyclic groups at the $R^1$ and $R^2$ positions may optionally be independently substituted with a divalent heteroatomic radical such as =O, =S, =NH, =NOH, and =NNH$_2$, wherein divalent heteroatomic radicals having one or more bound hydrogen atoms (i.e., hydrogen radicals), such as =NH, =NOH, and =NNH$_2$, optionally have these one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

When the point of attachment or bonding between the chalcone or chalcone derivative portion of the molecule, CHAL, and covalent bonding portion COV (optionally through linker portion LIN) occurs at one of the cyclic radicals $R^2$ or $R^1$ (as shown in Formulas (1a) and (1b), respectively), this attachment or bonding may occur at any ring position available for substitution (i.e., substitutable ring position, characterized by 1 or 2 bonds from a carbon or nitrogen ring member to a hydrogen). For example, when $R^2$ is an unsubstituted (i.e., hydrogen bearing) phenyl radical in Formula (1a), the linker portion of the molecule (when used) may be bonded to $R^2$ at any of five possible ring positions, as indicated in the structures below:

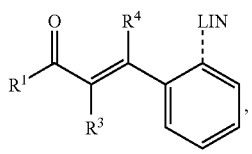

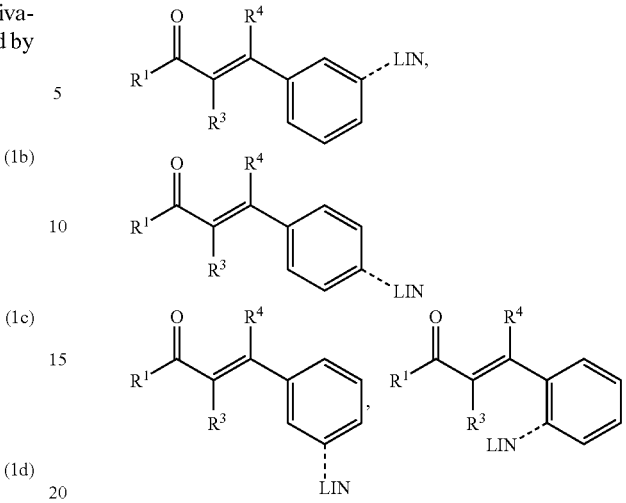

In this case, the four remaining substitutable ring positions (i.e., not substituted with the linker portion, LIN, or bonded to the rest of the chalcone or chalcone derivative portion of the molecule) may optionally be independently substituted with (A) a radical as defined for $R^3$ or $R^4$ below or (B) =O, =S, =NH, =NOH, and =NNH$_2$, wherein divalent heteroatomic radicals =NH, =NOH, and =NNH$_2$, optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

The same substitutions at substitutable ring positions of cyclic radicals $R^1$ and $R^2$ also apply to chalcone or chalcone derivative portions according to Formulas (1b), (1c), or (1d) above. The definitions of $R^3$ and $R^4$ below apply to the chalcone or chalcone derivative portion according to Formula (1b) above, the definitions of $R^4$ below apply to the chalcone or chalcone derivative portion according to Formula (1c) above, and the definitions of $R^3$ below apply to the chalcone or chalcone derivative portion according to Formula (1d) above.

In other embodiments of the invention, the —C(=O)—C=C— system of the parent chalcone may be incorporated into a fused ring structure. In these embodiments, CHAL has one of the Formulas (1a), (1b), or (1c) above, wherein $R^4$ is a methylene carbon atom (—CH$_2$—) of a ring that is fused to (i.e., has two shared ring atoms, such as two shared ring carbon atoms, with) $R^1$ and wherein $R^4$ is (X) optionally substituted with one or two radicals independently selected from alkyl, alkenyl, alkynyl, —OH, —SH, —SOH, —SO$_2$H, —SO$_3$H, —NH$_2$, —NO$_2$, —CO$_2$H, —CONH$_2$, —CN, —F, —Cl, —Br, or —I; (Y) optionally substituted with =O, =S, =NH, =NOH, and =NNH$_2$; or (Z) optionally replaced by —O—, —S—, —SO—, —SO$_2$—, or —NH—. Also, in these embodiments, $R^4$; the —C(=O)—C=C— system to which $R^1$ and $R^4$ are commonly bonded; optionally from 1 to 3 divalent radicals independently selected from —CH$_2$—, —O—, —S—, —SO—, —SO$_2$—, or —NH—; and the two shared ring atoms of $R^1$; form the ring that is fused to $R^1$. The ring that is fused to $R^1$ may be substituted at any substitutable ring position in the same manner as described above with respect to cyclic groups $R^1$ and $R^2$. Also, when CHAL is of the formula (1a) or (1b), then $R^2$ may be bonded to the ring that is fused to $R^1$ at any substitutable ring position. When CHAL is of the formula (1b), then the linker portion of the molecule (when used) may be bonded to $R^1$ at any substitutable ring position. Likewise, when CHAL is of the formula (1c), the linker portion of the molecule (when used) may be bonded to the ring that is fused to $R^1$ at any substitutable ring position.

Thus, the structures of Formulas (1a), (1b), or (1c) above may contain fused rings, as shown in the particular embodiments below, where CHAL is represented by the Formulas (1ai'), (1ai"), (1bi'), (1bi"), (1ci') and (1ci"):

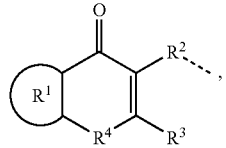
(1ai')

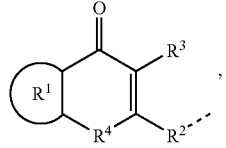
(1ai")

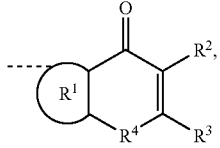
(1bi')

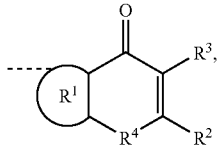
(1bi")

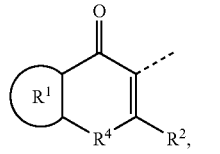
(1ci')

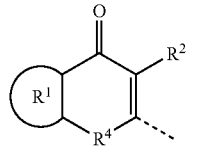
(1ci")

wherein $R^4$ is a methylene carbon atom (—CH$_2$—) which may be substituted or replaced as defined in (X), (Y), or (Z) above, and $R^2$ and $R^3$ are as defined in any of the embodiments described herein. In other embodiments, CHAL has a structure corresponding to any of the fused ring structures shown immediately above, wherein the C=C double bond to which $R^4$ is bonded is saturated to form a C—C single bond, thereby giving the structures (1aii'), (1aii"), (1bii'), (1bii"), (1cii') and (1cii"):

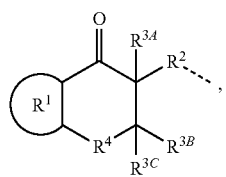
(1aii')

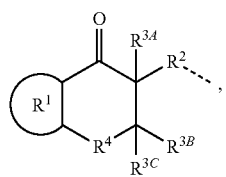
(1aii")

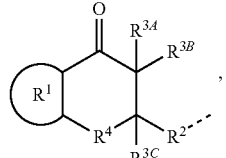
(1bii')

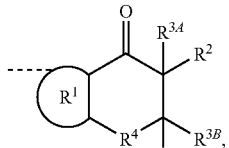
(1bii")

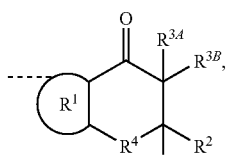
(1cii')

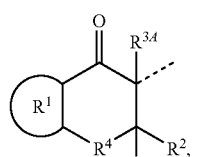
(1cii")

wherein $R^4$ is a methylene carbon atom (—CH$_2$—) which may be substituted or replaced as defined in (X), (Y), or (Z) above, $R^2$ is as defined in any of the embodiments described herein, and $R^{3A}$, $R^{3B}$, and $R^{3C}$ are independently selected from radicals as defined for $R^3$ according to any of the embodiments described herein.

Of particular interest are fused ring structures according to Formulas (1ai'), (1ai"), (1bi'), (1bi"), (1ci'), (1ci"), (1aii'), (1aii"), (1bii'), (1bii"), (1cii') and (1cii") above, wherein $R^1$ is phenyl, such that the fused ring structures shown in these formulas may be described as benzofused rings. In representative structures according to these embodiments, the group represented by CHAL may be a flavone or flavanone derivative of a chalcone, as described previously, having the $R^4$ methylene carbon atom (—CH$_2$—) in the fused ring structures above replaced by atom (—O—), to yield the following structures for CHAL:

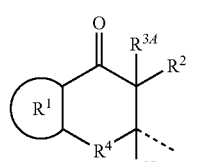

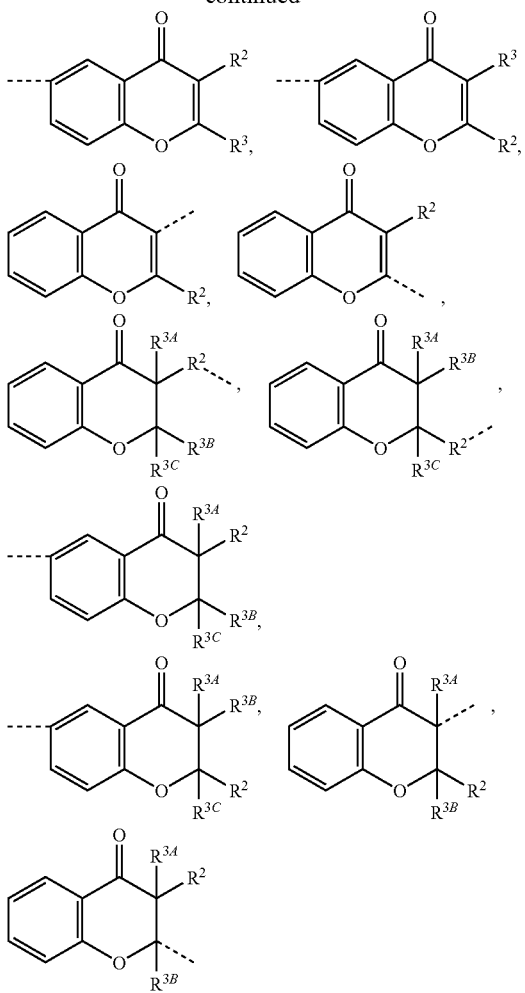

R³ and R⁴ are independently hydrogen radicals or saturated or partially unsaturated straight chain, branched, or cyclic hydrocarbon radicals having from 1 to about 20 carbon atoms, wherein (1) one or more carbon atoms having one or more bound hydrogen atoms (i.e., hydrogen radicals) are optionally substituted with a monovalent radical independently selected from alkyl, alkenyl, alkynyl, cycloalkyl, heterocycloalkyl, aryl, heteroaryl —OH, —SH, —SOH, —SO₂H, —SO₃H, —NH₂, —NO₂, —CO₂H, —CONH₂, —CN, —F, —Cl, —Br, and —I, wherein the monovalent heteroatomic radicals —OH, —SH, —SOH, —SO₂H, —SO₃H, —NH₂, —CO₂H, —CONH₂ optionally have one or more bound hydrogen atoms independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I;

(2) one or more carbon atoms having two or more bound hydrogen atoms are optionally substituted with a divalent radical independently selected from =O, =S, =NH, =NOH, and =NNH₂, wherein the divalent heteroatomic radicals =NH, =NOH, and =NNH₂ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I; and (3) one or more methylene carbon atoms (—CH₂—) are optionally replaced by a divalent radical independently selected from alkyl, alkenyl, alkynyl, cycloalkyl, heterocycloalkyl, aryl, heteroaryl, —O—, —S—, —NH—, —OCO—, —CO₂—, —CONH—, —OCONH—, and —CO₂NH—, wherein the divalent heteroatomic radicals —NH—, —CONH—, —OCONH—, and —CO₂NH— optionally have one or more hydrogen radicals independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I.

One or both of R³ and R⁴ may themselves also be independently selected from the monovalent heteroatomic radicals —OH, —SH, —SOH, —SO₂H, —SO₃H, —NH₂, —NO₂, —CO₂H, —CONH₂, —CN, —F, —Cl, —Br, and —I, wherein the monvalent heteroatomic radicals —OH, —SH, —SOH, —SO₂H, —SO₃H, —NH₂, —CO₂H, and —CONH₂ optionally have one or more hydrogen radicals independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I.

Representative R³ and R⁴ radicals therefore include hydrogen, alkyl, alkenyl, alkynyl, cycloalkyl, heterocycloalkyl, aryl, heteroaryl, (cycloalkyl)alkyl, (cycloalkyl)alkenyl, (cycloalkyl)alkynyl, (heterocycloalkyl)alkyl, (heterocycloalkyl)alkenyl, (heterocycloalkyl)alkynyl, aralkyl, aralkenyl, aralkynyl, heteroaralkyl, heteroaralkenyl, heteroaralkynyl, hydroxy, alkoxy, alkenoxy, alkynoxy, cycloalkoxy, heterocycloalkoxy, aryloxy, heteroaryloxy, hydroxyalkyl, hydroxyalkenyl, hydroxyalkynyl, hydroxy(cycloalkyl), hydroxy(heterocycloalkyl), hydroxy(aryl), hydroxy(heteroaryl), alkoxyalkyl, alkoxyalkenyl, alkoxyalkynyl, alkoxy(cycloalkyl), alkoxy(heterocycloalkyl), alkoxy(aryl), alkoxy(heteroaryl), alkenoxyalkyl, alkenoxyalkenyl, alkenoxyalkynyl, alkenoxy(cycloalkyl), alkenoxy(heterocycloalkyl), alkenoxy(aryl), alkenoxy(heteroaryl), alkynoxyalkyl, alkynoxyalkenyl, alkynoxyalkynyl, alkynoxy(cycloalkyl), alkynoxy(heterocycloalkyl), alkynoxy(aryl), alkynoxy(heteroaryl), cycloalkoxyalkyl, cycloalkoxyalkenyl, cycloalkoxyalkynyl, cycloalkoxy(cycloalkyl), cycloalkoxy(heterocycloalkyl), cycloalkoxy(aryl), cycloalkoxy(heteroaryl), heterocycloalkoxyalkyl, heterocycloalkoxyalkenyl, heterocycloalkoxyalkynyl, heterocycloalkoxy(cycloalkyl), heterocycloalkoxy(heterocycloalkyl), heterocycloalkoxy(aryl), heterocycloalkoxy(heteroaryl), aryloxyalkyl, aryloxyalkenyl, aryloxyalkynyl, aryloxy(cycloalkyl), aryloxy(heterocycloalkyl), aryloxy(aryl), aryloxy(heteroaryl), heteroaryloxyalkyl, heteroaryloxyalkenyl, heteroaryloxyalkynyl, heteroaryloxy(cycloalkyl), heteroaryloxy(heterocycloalkyl), heteroaryloxy(aryl), heteroaryloxy(heteroaryl), carbonyl, hydroxycarbonyl, hydroxycarbonylalkyl, hydroxycarbonylalkenyl, hydroxycarbonylalkynyl, hydroxycarbonyl(cycloalkyl), hydroxycarbonyl(heterocycloalkyl), hydroxycarbonyl(aryl), hydroxycarbonyl(heteroaryl), alkanoyl, alkenoyl, alkynoyl, cycloalkanoyl, heterocycloalkanoyl, aroyl, heteroaroyl, hydroxyalkanoyl, hydroxyalkenoyl, hydroxyalkynoyl, hydroxycycloalkanoyl, hydroxyheterocycloalkanoyl, hydroxyaroyl, hydroxyheteroaroyl, carbonyloxy, alkanoyloxy, alkenoyloxy, alkynoyloxy, cycloalkanoyloxy, heterocycloalkanoyloxy, aroyloxy, hetero aroyloxy, alkoxycarbonyl, alkenoxycarbonyl, alkynoxycarbonyl, cycloalkoxycarbonyl, heterocycloalkoxycarbonyl, aryloxycarbonyl, heteroaryloxycarbonyl, thiol, alkylthiol, alkenylthiol, alkynylthiol, thiolalkyl, thiolalkenyl, thiolalkynyl, amino, alkylamino, alkenylamino, alkynylamido, (cycloalkyl)amino, (heterocycloalkyl)amino, arylamino, (heteroaryl) amino, hydroxyamino, alkoxyamino, alkenoxyamino, alkynoxyamino, cycloalkoxyamino, heterocycloalkoxyamino, aryloxyamino, heteroaryloxyamino, aminocarbonyl, aminocarbonylalkyl, aminocarbonylalkenyl, aminocarbonylalkynyl, aminocarbonyl(cycloalkyl), aminocarbonyl(heterocycloalkyl), aminocarbonyl(aryl), aminocarbonyl(heteroaryl), halo, haloalkyl, haloalkenyl, haloalkynyl, halo(cycloalkyl), halo(heterocycloalkyl), halo (aryl), halo(heteroaryl), amido, alkylamido, alkenylamido, alkynylamido, (cycloalkyl)amido, (heterocycloalkyl)amido, arylamido, (heteroaryl)amido, hydroxyamido, alkoxyamido, alkenoxyamido, alkynoxyamido, cycloalkoxyamido, heterocycloalkoxyamido, aryloxyamido, and heteroaryloxyamido.

In another embodiment, $R^3$ and $R^4$ are independently selected from a more specific group of radicals consisting of hydrogen, alkyl, alkenyl, alkynyl, cycloalkyl, heterocycloalkyl, aryl, heteroaryl, (cycloalkyl)alkyl, (heterocycloalkyl)alkyl, aralkyl, heteroaralkyl, hydroxy, alkoxy, cycloalkoxy, aryloxy, hydroxycarbonyl, hydroxycarbonylalkyl, alkanoyl, alkanoyloxy, alkoxycarbonyl, thiol, alkylthiol, amino, halo, haloalkyl, amido, alkylamido, (cycloalkyl) amido, (heterocycloalkyl)amido, arylamido, and (heteroaryl) amido.

In another embodiment, the optional substituents for the cyclic radicals $R^1$ and $R^2$ (i.e., cycloalkyl, heterocycloalkyl, aryl, or heteroaryl) at one or more substitutable ring positions are independently selected from a more specific group of radicals consisting of alkyl, alkenyl, alkynyl, cycloalkyl, heterocycloalkyl, aryl, heteroaryl, (cycloalkyl)alkyl, (heterocycloalkyl)alkyl, aralkyl, heteroaralkyl, hydroxy, alkoxy, cycloalkoxy, aryloxy, hydroxycarbonyl, hydroxycarbonylalkyl, alkanoyl, alkanoyloxy, alkoxycarbonyl, thiol, alkylthiol, amino, halo, haloalkyl, amido, alkylamido, (cycloalkyl) amido, (heterocycloalkyl)amido, arylamido, and (heteroaryl) amido.

In another embodiment, $R^3$ and $R^4$ are independently selected from a more specific group of radicals consisting of hydrogen, hydroxy, and alkoxy (e.g., methoxy, ethoxy, propoxy, etc.).

In another embodiment, the optional substituents for the cyclic radicals $R^1$ and $R^2$ at one or more substitutable ring positions are independently selected from a more specific group of radicals consisting of hydroxy and alkoxy (e.g., methoxy, ethoxy, propoxy, etc.).

In another embodiment, $R^3$ and $R^4$ are selected from a more specific group of radicals consisting of hydrogen and alkyl (e.g., methyl, ethyl, propyl, etc.).

In another embodiment, $R^1$ and $R^2$ are independently selected from a more specific group of radicals consisting of aryl or heteroaryl which may optionally be independently substituted at one or more substitutable ring positions with radicals according to any of the $R^1$ and $R^2$ optional substituent definitions or any of the $R^3$ and $R^4$ definitions provided herein.

In another embodiment, $R^1$ and $R^2$ are independently selected from a more specific group of aryl radicals consisting of phenyl and naphthyl, or from a more specific group of heteroaryl radicals selected from pyridyl, pyrrolyl, pyrazolyl, pyrimidinyl, triazolyl, pyrazinyl, pyranyl, furyl, dioxolyl, thienyl, thiazolyl, imidazolyl, imidazonolyl, oxazolyl, isoxazolyl, quinolinyl, isoquinolinyl, tetrahydroquinolinyl, tetrahydroisoquinolinyl, indolyl, isoindolyl, benzopyrazolyl, benzopyrimidinyl, benzotriazolyl, quinoxalinyl, benzopyranyl, benzofuryl, 2,3-dihydrobenzofuranyl, 2-benzofurancarbonyl, 1,3-benzodioxolyl, 1,4-benzodioxanyl, methylenedioxyphen-4-yl, methylenedioxyphen-5-yl, ethylenedioxyphenyl benzothienyl, benzothiazolyl, benzimidazolyl, benzimidazolonyl, benzoxazolyl, benisoxazolyl, and piperazinylphenyl, which aryl or heteroaryl radicals are optionally substituted at one or more substitutable ring positions with radicals according to any of the $R^1$ and $R^2$ optional substituent definitions or any of the $R^3$ and $R^4$ definitions provided herein.

In another embodiment, $R^1$ and $R^2$ are independently selected from a more specific group of aryl and heteroaryl radicals consisting of phenyl, pyridyl, furyl, thienyl, quinolinyl, and indolyl, which radicals are optionally substituted at one or more substitutable ring positions with radicals independently selected from hydroxy and alkoxy.

In other embodiments, one or both of $R^1$ and $R^2$ may independently be selected from heterocycloalkyl radicals including pyrrolidinyl, pyrazolidinyl, piperidinyl, piperazinyl, morpholinyl, thiamorpholinyl, dioxanyl, dioxolanyl, tetrahydrofuranyl, tetrahydrothienyl, tetrahydrothiopyranyl, which heterocycloalkyl radicals are optionally substituted at one or more substitutable ring positions with radicals according to any of the $R^1$ and $R^2$ optional substituent definitions or any of the $R^3$ and $R^4$ definitions provided herein.

Linker Portion (LIN)

As stated above, an optional linker portion LIN may be incorporated into the antimitotic agent to adjust the spatial arrangement (e.g., distance and direction from the chalcone or chalcone derivative portion), reactivity, and/or stability of the covalent bonding portion. Different target cellular mitotic agents (e.g., tubulin) having different regions for (a) association with the chalcone or chalcone derivative portion and/or (b) nucleophilic attack on the covalent binding portion may require different linker portions, as will be appreciated by those having skill in the art, in view of the present disclosure.

The linker portion may be selected from saturated or partially unsaturated straight chain, branched, or cyclic hydrocarbon radicals having from 1 to about 40 carbon atoms, wherein (1) one or more carbon atoms having one or more bound hydrogen atoms (i.e., hydrogen radicals) are optionally substituted with a monovalent radical independently selected from alkyl, alkenyl, alkynyl, cycloalkyl, heterocycloalkyl, aryl, heteroaryl —OH, —SH, —SOH, —SO$_2$H, —SO$_3$H, —NH$_2$, —NO$_2$, —CO$_2$H, —CONH$_2$, —CN, —F, —Cl, —Br, and —I, wherein the monovalent heteroatomic radicals —OH, —SH, —SOH, —SO$_2$H, —SO$_3$H, —NH$_2$, —CO$_2$H, —CONH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;

(2) one or more carbon atoms having two or more bound hydrogen atoms (i.e., hydrogen radicals) are optionally substituted with a divalent radical independently selected from =O, =S, =NH, =NOH, and =NNH$_2$, wherein the divalent heteroatomic radicals =NH, =NOH, and =NNH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by a divalent radical independently selected from alkyl, alkenyl, alkynyl, cycloalkyl, heterocycloalkyl, aryl, heteroaryl, —O—, —S—, —NH—, —OCO—, —CO$_2$—, —CONH—, —OCONH—, and —CO$_2$NH—, wherein the divalent heteroatomic radicals —NH—, —CONH—, —OCONH—, and —CO₂NH— optionally have one or more hydrogen radicals independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I.

Representative linker portions include the divalent heteroatomic radicals oxycarbonyl, (secondary)aminocarbonyl, and (mercapto)carbonyl structures below:

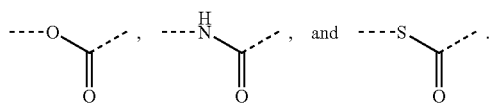

with dashed lines indicating the points of attachment or bonding between the linker portion -LIN- and (A) the chalcone or chalcone derivative portion CHAL- and (B) the covalent bonding portion -COV, as shown above in Formula I. CHAL and COV may be bonded at the left-hand and right-hand points of attachment, respectively, of these divalent heteroatomic radicals, or vice versa. In preferred embodiments, CHAL is bonded at the left-hand point of attachment and COV is bonded at the right-hand point of attachment. In any of the above representative linker portions, the carbonyl oxygen atom (=O) may be replaced by other divalent heteroatomic radicals such as =NH or =S or any of the other radicals as described under (2) above in the definition of the linker portion.

In representative linker portions, the divalent heteroatomic radical structures (oxycarbonyl, (secondary)aminocarbonyl, and (mercapto)carbonyl), indicated above, may be directly bonded to either or both of the chalcone or chalcone derivative portion and the covalent bonding portion. Alternatively, these divalent heteroatomic radical structures may be spaced apart from either or both of the chalcone or chalcone derivative portion and the covalent bonding portion using hydrocarbon or substituted hydrocarbon radicals bonded to one or both ends of the structures. The hydrocarbon or substituted hydrocarbon radicals, when present, may be made more rigid through the use of one or more sites of unsaturation (i.e., carbon-carbon double bonds or carbon-carbon triple bonds).

Thus, in other embodiments, the divalent heteroatomic radical structures (oxycarbonyl, (secondary)aminocarbonyl, and (mercapto)carbonyl), indicated above, may be preceded and/or followed by a saturated or partially unsaturated straight chain hydrocarbon radical having from 1 to about 20 carbon atoms, wherein each of these hydrocarbon radicals may have carbon atoms substituted or replaced as described under (1), (2), and (3) above in the definition of the linker portion.

Preferred linker portions are selected from -alkoxycarbonylalkyl-, -alkenoxycarbonylalkyl-, -alkynyloxycarbonylalkyl-, -alkoxycarbonylalkenyl-, -alkenoxycarbonylalkenyl-, -alkynyloxycarbonylalkenyl-, -alkoxycarbonylalkynyl-, -alkenoxycarbonylalkynyl-, -alkynyloxycarbonylalkynyl-, -alkylaminocarbonylalkyl-, -alkenylaminocarbonylalkyl-, -alkynylaminocarbonylalkyl-, -alkylaminocarbonylalkenyl-, -alkenylaminocarbonylalkenyl-, -alkynylaminocarbonylalkenyl-, -alkylaminocarbonylalkynyl-, -alkenylaminocarbonylalkynyl-, -alkynylaminocarbonylalkynyl-, -(alkylthiol)carbonylalkyl-, -(alkenylthiol)carbonylalkyl-, -(alkynylthiol)carbonylalkyl-, -(alkylthiol)carbonylalkenyl-, -(alkenylthiol) carbonylalkenyl-, -(alkynylthiol)carbonylalkenyl-, -(alkylthiol)carbonylalkynyl-, -(alkenylthiol)carbonylalkynyl-, -(alkynylthiol)carbonylalkynyl-, -alkoxyiminoalkyl-, -alkenoxyiminoalkyl-, -alkynoxyiminoalkyl-, -alkoxyiminoalkenyl-, -alkenoxyiminoalkenyl-, -alkynoxyiminoalkenyl-, -alkoxyiminoalkynyl-, -alkenoxyiminoalkynyl-, -alkynoxyiminoalkynyl-, -alkylaminoiminoalkyl-, -alkenylaminoiminoalkyl-, -alkynylaminoiminoalkyl-, -alkylaminoiminoalkenyl-, -alkenylaminoiminoalkenyl-, -alkynylaminoiminoalkenyl-, -alkylaminoiminoalkynyl-, -alkenylaminoiminoalkynyl-, -alkynylaminoiminoalkynyl-, -alkylthioliminoalkyl-, -alkenylthioliminoalkyl-, -alkynylthioliminoalkyl-, -alkylthioliminoalkenyl-, -alkenylthioliminoalkenyl-, -alkynylthioliminoalkenyl-, -alkylthioliminoalkynyl-, -alkenylthioliminoalkynyl-, -alkynylthioliminoalkynyl-, -alkoxy(thiocarbonyl)alkyl-, -alkenoxy(thiocarbonyl)alkyl-, -alkynoxy(thiocarbonyl)alkyl-, -alkoxy(thiocarbonyl)alkenyl-, -alkenoxy(thiocarbonyl)alkenyl-, -alkynoxy(thiocarbonyl)alkenyl-, -alkoxy(thiocarbonyl)alkynyl-, -alkenoxy(thiocarbonyl)alkynyl-, -alkynoxy(thiocarbonyl)alkynyl-, -alkylamino(thiocarbonyl) alkyl-, -alkenylamino(thiocarbonyl)alkyl-, -alkynylamino(thiocarbonyl)alkyl-, -alkylamino(thiocarbonyl)alkenyl-, -alkenylamino(thiocarbonyl)alkenyl-, -alkynylamino(thiocarbonyl)alkenyl-, -alkylamino(thiocarbonyl)alkynyl-, -alkenylamino(thiocarbonyl)alkynyl-, -alkynylamino(thiocarbonyl)alkynyl-, -alkylthiol(thiocarbonyl)alkyl-, -alkenylthiol(thiocarbonyl)alkyl-, -alkynylthiol(thiocarbonyl)alkyl-, -alkylthiol(thiocarbonyl)alkenyl-, -alkenylthiol(thiocarbonyl)alkenyl-, -alkynylthiol(thiocarbonyl)alkenyl-, -alkylthiol(thiocarbonyl)alkynyl-, -alkenylthiol(thiocarbonyl)alkynyl-, and -alkynylthiol(thiocarbonyl)alkynyl-, wherein alkyl, alkenyl, alkynyl, and the alkyl, alkenyl, and alkynyl portions of alkoxy, alkenoxy, alkynoxy, alkylamino, alkenylamino, alkynylamino, alkylthiol, alkenylthiol, or alkynylthiol independently have from 0 to about 20 carbon atoms, wherein (i) one or more carbon atoms having one or more bound hydrogen atoms (i.e., hydrogen radicals) are optionally substituted with a monovalent radical independently selected from alkyl having 1-3 carbon atoms, alkenyl having 1-3 carbon atoms, alkynyl having 1-3 carbon atoms, hydroxy, and alkyoxy having 1-3 alkyl carbon atoms;

(ii) one or more carbon atoms having two or more bound hydrogen atoms are optionally substituted with a divalent radical independently selected from =O, =S, and =NH; and (iii) one or more methylene carbon atoms (—CH₂—) are optionally replaced by a divalent radical independently selected from —O—, —NH—, or —S—.

In the preferred linker portions described above, when alkyl, alkenyl, or alkynyl have 0 carbon atoms, the linker is bonded via a carbonyl carbon atom, a thiocarbonyl carbon atom, or an imino carbon atom to either (A) the chalcone or chalcone derivative portion or (B) the covalent bonding portion of the molecule. Likewise, when the alkyl, alkenyl, or alkynyl portions of alkoxy, alkenoxy, alkynoxy, alkylamino, alkenylamino, alkynylamino, alkylthiol, alkenylthiol, or alkynylthiol in the preferred linker portions described above have 0 carbon atoms, the linker is bonded directly via a heteroatom (O, N, or S) to either (A) the chalcone or chalcone derivative portion or (B) the covalent bonding portion of the molecule.

Particular embodiments wherein alkyl, alkenyl, and alkynyl portions of alkoxy, alkenoxy, alkynoxy, alkylamino, alkenylamino, alkynylamino, alkylthiol, alkenylthiol, or alkynylthiol have 0 carbon atoms include the linker portions -oxycarbonylalkyl-, -(secondary)aminocarbonylalkyl-, and -(thiol)carbonylalkyl-, -oxy(thiocarbonyl)alkyl-, -(secondary)amino(thiocarbonyl)alkyl-, -(thiol)(thiocarbonyl)alkyl-, -oxyiminoalkyl-, -(secondary)aminoiminoalkyl-, and -(thiol)iminoalkyl-, having the structures below:

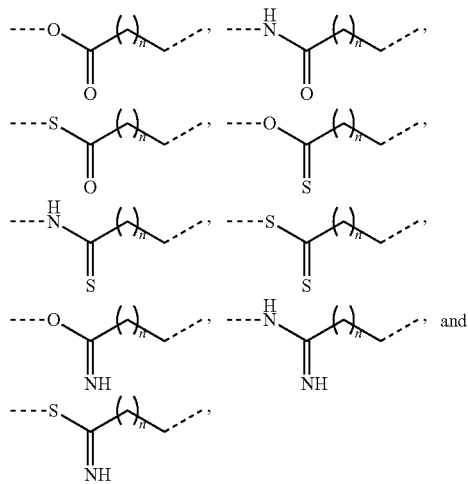

wherein n is from 0 to about 20, and often from 0 to about 5, and the alkyl carbon atoms may be substituted and/or replaced as described in (i), (ii), and (iii) above.

Specific linker portions according to the above embodiments are derived from acetic acid and propanoic acid, as shown in the structures below, respectively:

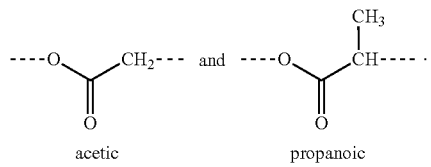

acetic        propanoic wherein the stereocenter (C-2 in the latter, propanoic acid derived structure) may be enriched to a desired ratio of, or purified with respect to, its (R) or (S) stereoisomer by use of reactants of desired enantiomeric purity during synthesis or by stereochemical purification techniques (e.g., resolution of enantiomers via chromatography with chiral stationary phases).

In other embodiments, linker portions may include hydrocarbon radicals at both ends of the divalent heteroatomic radicals described above, but may also include a direct heteroatom linkage (e.g., through —O—, —NH—, or —S—) to either or both of (A) the chalcone or chalcone derivative portion and (B) the covalent bonding portion of the molecule. In these embodiments, alkyl, alkenyl, alkynyl, and the alkyl, alkenyl, and alkynyl portions of alkoxy, alkenoxy, alkynoxy, alkylamino, alkenylamino, alkynylamino, alkylthiol, alkenylthiol, and alkynylthiol independently have from 1 to about 20 carbon atoms, wherein (a) one or more carbon atoms having one or more bound hydrogen atoms (i.e., hydrogen radicals) are optionally substituted with methyl or ethyl radicals;

(b) one or more carbon atoms having two or more bound hydrogen atoms (i.e., hydrogen radicals) are optionally substituted with =O; and (c) either (I) the carbon atom of the alkyl, alkenyl, or alkynyl portion of alkoxy, alkenoxy, alkynoxy, alkylamino, alkenylamino, alkynylamino, alkylthiol, alkenylthiol, and alkynylthiol that is adjacent to CHAL or COV in Formula I or (II) the carbon atom of alkyl, alkenyl, or alkynyl, that is adjacent to either CHAL or COV in Formula I or (III) both carbon atoms (I) and (II) are replaced by a divalent radical independently selected from —O—, —NH—, and —S—.

Covalent Bonding Portion (COV)

As described above, the covalent bonding portion of the antimitotic agent can irreversibly inactivate a target biomolecule through a number of potential reaction pathways, including addition of nucleophilic groups (e.g., sulfhydryl groups) of the target to electrophilic groups of the antimitotic agent. The covalent bonding portion is bonded to the chalcone or chalcone derivative portion, often through the linker portion, with a divalent heteroatomic radical that is in turn bonded to a hydrocarbon radical.

Suitable covalent bonding portions therefore include -oxycarbonylalkyl, -oxycarbonylalkenyl, -oxycarbonylalkynyl, -(secondary)aminocarbonylalkyl, -(secondary)aminocarbonylalkenyl, -(secondary)aminocarbonylalkynyl, -(thiol)carbonylalkyl, -(thiol)carbonylalkenyl, -(thiol)carbonylalkynyl, -oxy(thiocarbonyl)alkyl, -oxy(thiocarbonyl)alkenyl, -oxy(thiocarbonyl)alkynyl, -(secondary)amino(thiocarbonyl)alkyl, -(secondary)amino(thiocarbonyl)alkenyl, -(secondary)amino(thiocarbonyl)alkynyl, -(thiol)(thiocarbonyl)alkyl, -(thiol)(thiocarbonyl)alkenyl, -(thiol)(thiocarbonyl)alkynyl, -oxyiminoalkyl, -oxyiminoalkenyl, -oxyiminoalkynyl, -(secondary)aminoiminoalkyl, -(secondary)aminoiminoalkenyl, -(secondary)aminoiminoalkynyl, -(thiol)iminoalkyl, -(thiol)iminoalkenyl, -(thiol)iminoalkynyl, wherein alkyl, alkenyl, and alkynyl have from 0 to about 20 carbon atoms, wherein (1) one or more carbon atoms having one or more bound hydrogen atoms (i.e., hydrogen radicals) are optionally substituted with a monovalent radical independently selected from alkyl, alkenyl, alkynyl, cycloalkyl, heterocycloalkyl, aryl, heteroaryl —OH, —SH, —SOH, —SO$_2$H, —SO$_3$H, —NH$_2$, —NO$_2$, —CO$_2$H, —CONH$_2$, —CN, —F, —Cl, —Br, and —I, wherein the monovalent heteroatomic radicals —OH, —SH, —SOH, —SO$_2$H, —SO$_3$H, —NH$_2$, —CO$_2$H, —CONH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;

(2) one or more carbon atoms having two or more bound hydrogen atoms are optionally substituted with a divalent radical independently selected from =O, =S, =NH, =NOH, and =NNH$_2$, wherein the divalent heteroatomic radicals =NH, =NOH, and =NNH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by a divalent radical independently selected from alkyl, alkenyl, alkynyl, cycloalkyl, heterocycloalkyl, aryl, heteroaryl, —O—, —S—, —NH—, —OCO—, —CO$_2$—, —CONH—, —OCONH—, and —CO$_2$NH—, wherein the divalent heteroatomic radicals —NH—, —CONH—, —OCONH—, and —CO$_2$NH— optionally have one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

Preferred covalent bonding portions include those described above wherein the hydrocarbon radical bonded to the divalent heteroatomic radical is alkenyl. Such covalent bonding portions therefore include -oxycarbonylalkenyl, -(secondary)aminocarbonylalkenyl, -(thiol)carbonylalkenyl, -oxy(thiocarbonyl)alkenyl, -(secondary)amino(thiocarbonyl)alkenyl, -(secondary)amino(thiocarbonyl)alkenyl, -(thiol)(thiocarbonyl)alkenyl, -oxyiminoalkenyl, -(secondary)aminoiminoalkenyl, -(thiol)iminoalkenyl, wherein alkenyl has from 0 to about 10 carbon atoms which may be substituted or replaced as described under (1), (2), and (3) above in the definition of the covalent bonding portion.

Another class of covalent bonding portions include those wherein the hydrocarbon radical bonded to the divalent heteroatomic radical is alkenyl, and a double bond exists between the α- and β-carbon atoms, in relation to the divalent heteroatomic radical. These covalent bonding portions are represented by the structures below:

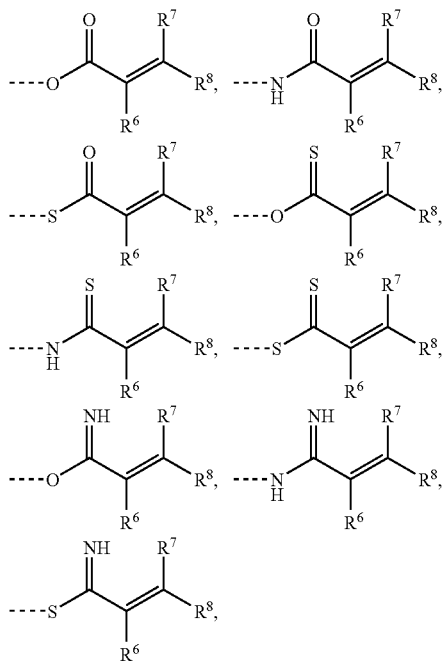

with dashed lines indicating the points of attachment or bonding between the covalent bonding portion -COV and the chalcone or chalcone derivative portion CHAL-, optionally through linker portion -LIN-, as shown above in Formula I. $R^6$, $R^7$, and $R^8$ independently represent radicals according to any of the definitions for $R^3$ and $R^4$ above with respect to the chalcone or chalcone derivative portion CHAL.

Particular covalent bonding groups of interest include α,β-unsaturated thiol ester groups having the Formula (COV1) below:

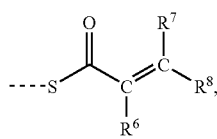

(COV1)

wherein $R^6$, $R^7$, and $R^8$ independently represent radicals according to any of the definitions for $R^3$ and $R^4$ above with respect to the chalcone or chalcone derivative portion CHAL.

Other specific classes of α,β-unsaturated thiol ester groups, which overlap with the α,β-unsaturated thiol ester groups described immediately above (e.g., in cases where $R^8$ in the formula shown immediately above is alkenyl or substituted alkenyl having a conjugated double bond system comprising 2 or 3 consecutive occurrences of a C=C double bond adjacent to a C—C single bond), include the covalent bonding portions having the structures below:

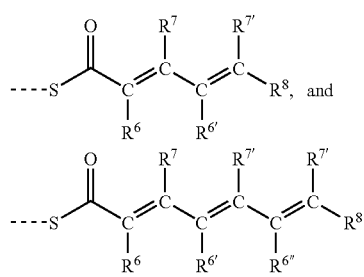

wherein $R^6$, $R^7$, $R^{6'}$, $R^{7'}$, $R^{6''}$, $R^{7''}$, and $R^8$ independently represent radicals according to any of the definitions for $R^3$ and $R^4$ above with respect to the chalcone or chalcone derivative portion CHAL.

In the immediately preceding structures, $R^8$ may be defined as having fewer carbon atoms (e.g., from 0 to about 10 carbon atoms) than defined in Formula (COV1) above, such that these structures are all within the scope of Formula (COV1). In particular, $R^8$ may be a hydrogen radical or a saturated or partially unsaturated straight chain, branched, or cyclic hydrocarbon radical having from 1 to about 10 carbon atoms, wherein (1) one or more carbon atoms having one or more bound hydrogen atoms are optionally independently substituted with alkyl, alkenyl, alkynyl, cycloalkyl, heterocycloalkyl, aryl, heteroaryl —OH, —SH, —SOH, —SO$_2$H, —SO$_3$H, —NH$_2$, —NO$_2$, —CO$_2$H, —CONH$_2$, —CN, —F, —Cl, —Br, or —I, wherein —OH, —SH, —SOH, —SO$_2$H, —SO$_3$H, —NH$_2$, —CO$_2$H, or —CONH$_2$ optionally has one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;

(2) one or more carbon atoms having two or more bound hydrogen atoms are optionally independently substituted with =O, =S, =NH, =NOH, or =NNH$_2$, wherein =NH, =NOH, or =NNH$_2$ optionally has one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by alkyl, alkenyl, alkynyl, cycloalkyl, heterocycloalkyl, aryl, heteroaryl, —O—, —S—, NH—, —OCO—, —CO$_2$—, —CONH—, —OCONH—, or —CO$_2$NH—, wherein —NH—, —CONH—, —OCONH—, or —CO$_2$NH— optionally has one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I, or $R^8$ is independently selected from the group consisting of —OH, —SH, —SOH, —SO$_2$H, —SO$_3$H, —NH$_2$, —NO$_2$, —CO$_2$H, —CONH$_2$, —CN, —F, —Cl, —Br, and —I, wherein —OH, —SH, —SOH, —SO$_2$H, —SO$_3$H, —NH$_2$, —CO$_2$H, or —CONH$_2$ optionally has one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

Particular Classes of Antimitotic Agents

In view of the above, particular classes of antimitotic agents of the general Formula I:

CHAL-LIN-COV          (I)

have the structural formulas given below:

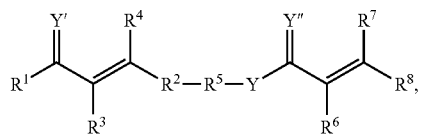

(1a')

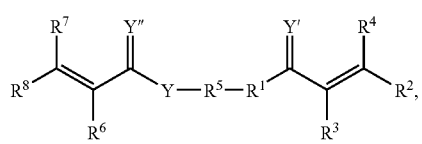

(1b')

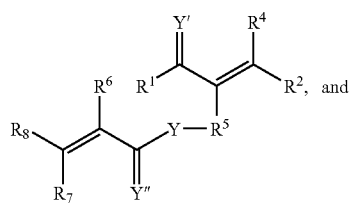

(1c')

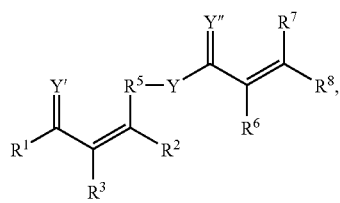

(1d')

wherein Formulas (1a'), (1b'), (1c'), and (1d') represent specific structures within the classes of compounds represented by Formulas (1a), (1b), (1c), and (1d), above, respectively. The variables $R^1$-$R^4$ and $R^6$-$R^8$ are as defined herein, the variables Y, Y', and Y" independently represent a divalent heteroatomic radical selected from =O, =NH, and =S, and the variable $R^5$ represents a bond or an optional linker portion as defined herein.

More specific classes of antimitotic agents are obtained when Y is —S—, and Y' and Y" are both =O. These classes are represented by Formulas (1a"), (1b"), (1c"), and (1d") below:

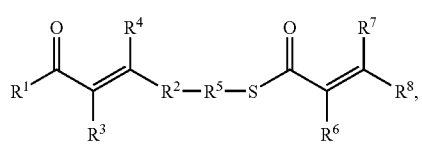

(1a")

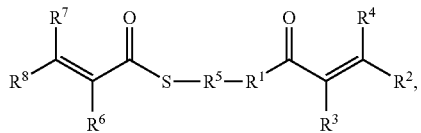

(1b")

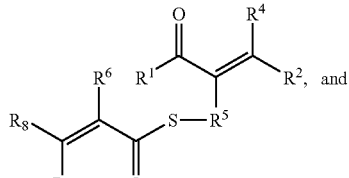

(1c")

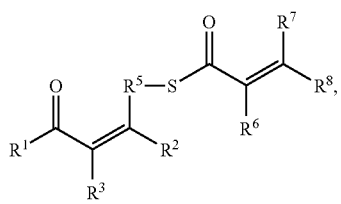

(1d")

A particular compound within the scope of Formula (1a") above, for example, includes 3-[3-(crotonylsulfanylmethylcarbonyloxy)-4-methoxyphenyl]-1-(3,4,5-trimethoxyphenyl)propenone (CMAC-1), having the structure

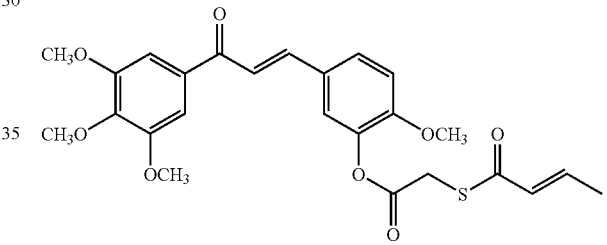

wherein $R^1$ is 3,4,5-trimethoxyphenyl; $R^2$ is 4-methoxyphenyl; $R^3$, $R^4$, $R^6$, and $R^7$ are hydrogen; $R^5$ is -oxycarbonylmethyl-(—O—C(=O)—CH$_2$—); and $R^8$ is methyl.

Another particular compound of Formula (1a") includes 3-[5-(crotonylsulfanylmethylcarbonyloxymethyl)-2-furyl]-1-(3,4,5-trimethoxyphenyl)propenone (CMAF-1), having the structure

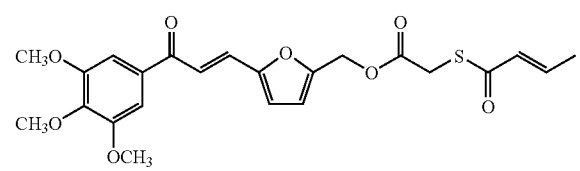

wherein $R^1$ is 3,4,5-trimethoxyphenyl; $R^2$ is furyl; $R^3$, $R^4$, $R^6$, and $R^7$ are hydrogen; $R^5$ is -methoxycarbonylmethyl-(—CH$_2$—O—C(=O)—CH$_2$—); and $R^8$ is methyl.

The compounds 3-[6-(crotonylsulfanylmethylcarbonyloxymethyl)-2-pyridyl]-1-(3,4,5-trimethoxyphenyl)propenone and 3-[5-(crotonylsulfanylmethylcarbonyloxymethyl)-3-(1H-indol-3-yl)]-1-(3,4,5-trimethoxyphenyl)propenone are obtained when the furyl radical (represented by $R^2$ in Formula (1a")) in the above compound is replaced by $R^2$ radicals of pyridyl or indolyl. These compounds have the structural formulas below, respectively:

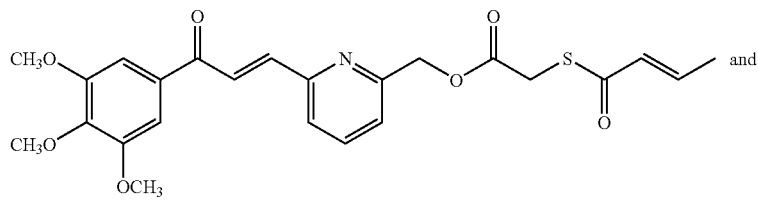
and
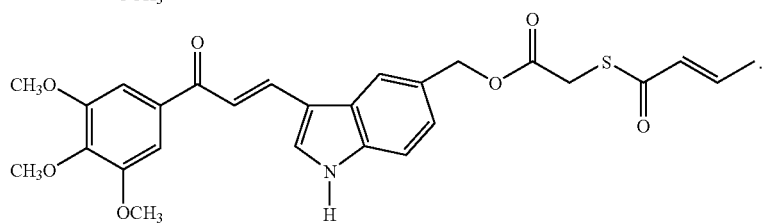
Examples of specific compounds of Formula I:
CHAL-LIN-COV    (I)
that are within the scope of the present invention are provided in Table 1, below:
TABLE 1
Examples of Antimitotic Agents of the Formula CHAL-LIN-COV (Formula I)
| Entry | CHAL- | -LIN- | -COV |
|---|---|---|---|
| 1 | | | |
| 2 | | | |
| 3 | | | |
| 4 | | | |

TABLE 1-continued

Examples of Antimitotic Agents of the Formula CHAL-LIN-COV (Formula I)

| Entry | CHAL- | -LIN- | -COV |
|---|---|---|---|
| 5 | 3,4,5-trimethoxyphenyl-CO-CH=CH-(4-methoxyphenyl)- | ----O-CH₂-CH₂-O-C(=O)-CH₂---- | ----S-C(=O)-C(CH₃)=CH- (E) |
| 6 | 3,4,5-trimethoxyphenyl-CO-CH=CH-(4-methoxyphenyl)- | — | ----O-C(=O)-C(Cl)=CH₂ |
| 7 | 3,4,5-trimethoxyphenyl-CO-CH=CH-(4-methoxyphenyl)- | — | ----O-C(=O)-C(Br)=CH₂ |
| 8 | 3,4,5-trimethoxyphenyl-CO-CH=CH-(4-methoxyphenyl)- | ----O-CH₂-CH₂---- | ----S-C(=O)-C(Cl)=CH₂ |
| 9 | 3,4,5-trimethoxyphenyl-CO-CH=CH-(4-methoxyphenyl)- | ----O-C(=O)-CH₂-CH₂---- | ----S-C(=O)-C(CH₃)=CH- (E) |
| 10 | 3,4,5-trimethoxyphenyl-CO-CH=CH-(3,4-dimethoxyphenyl)- | ----NH-C(=O)-CH₂---- | ----S-C(=O)-C(CH₃)=CH- (E) |
| 11 | 3,4,5-trimethoxyphenyl-CO-CH=CH-(furan-2,5-diyl)- | ----O-C(=O)-CH₂---- | ----S-C(=O)-C(CH₃)=CH- (E) |

TABLE 1-continued

Examples of Antimitotic Agents of the Formula CHAL-LIN-COV (Formula I)

| Entry | CHAL- | -LIN- | -COV |
|---|---|---|---|
| 12 | 2,4-dimethoxyphenyl chalcone with 4-Br phenyl | –O–C(=O)–CH$_2$– | –S–C(=O)–CH=CH–CH$_3$ |
| 13 | 2,4-dimethoxyphenyl chalcone with 2,3-dimethoxyphenyl | –O–C(=O)–CH$_2$– | –S–C(=O)–CH=CH–CH$_3$ |
| 14 | 2,4-dimethoxyphenyl chalcone with 4-Br phenyl | –O–C(=O)–CH(CH$_3$)– | –S–C(=O)–CH=CH–CH$_3$ |
| 15 | 2,4-dimethoxyphenyl chalcone with 2-furyl | –O–C(=O)–CH$_2$– | –S–C(=O)–CH=CH–CH$_3$ |
| 16 | 2,4-dimethoxyphenyl chalcone with 2-thienyl | –O–C(=O)–CH$_2$– | –S–C(=O)–CH=CH–CH$_3$ |
| 17 | 2,4-dimethoxyphenyl chalcone with 4-pyridyl | –O–C(=O)–CH$_2$– | –S–C(=O)–CH=CH–CH$_3$ |
| 18 | 2,4-dimethoxyphenyl chalcone with 3-pyridyl | –O–C(=O)–CH$_2$– | –S–C(=O)–CH=CH–CH$_3$ |
| 19 | 2,4-dimethoxyphenyl chalcone with 3-indolyl | –O–C(=O)–CH$_2$– | –S–C(=O)–CH=CH–CH$_3$ |
| 20 | 2,4-dimethoxyphenyl chalcone with 2-quinolyl | –O–C(=O)–CH$_2$– | –S–C(=O)–CH=CH–CH$_3$ |

TABLE 1-continued
Examples of Antimitotic Agents of the Formula CHAL-LIN-COV (Formula I)
| Entry | CHAL- | -LIN- | -COV |
|---|---|---|---|
| 21 | 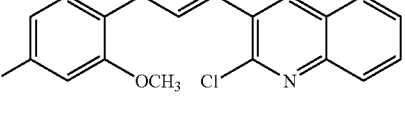 | 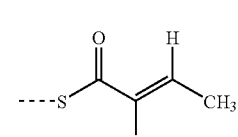 | 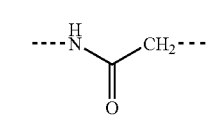 |
| 22 | 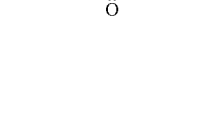 | 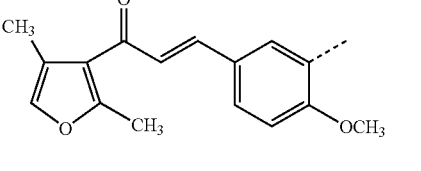 | 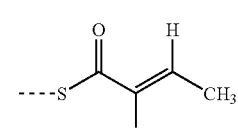 |
| 23 | 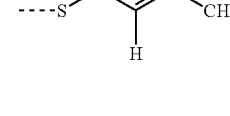 | 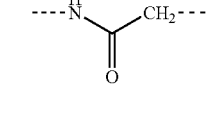 | 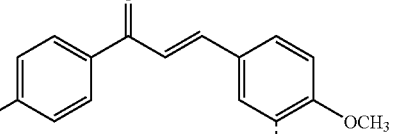 |
| 24 | 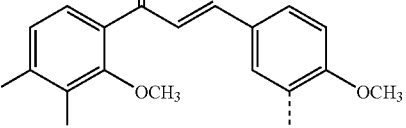 | 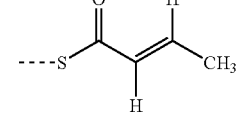 | 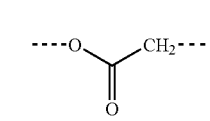 |
| 25 | 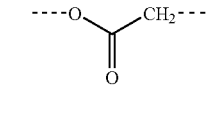 | 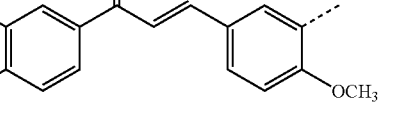 | 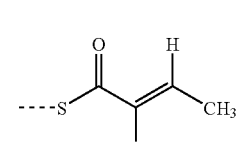 |
| 26 | 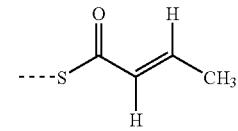 | 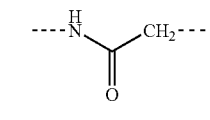 | 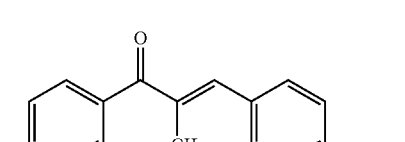 |
| 27 | 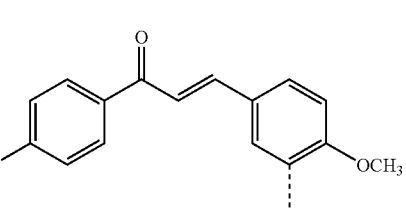 | 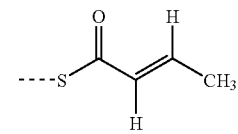 | 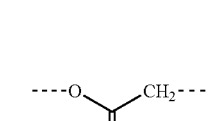 |
| 28 | 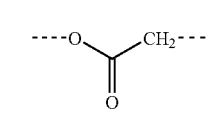 | 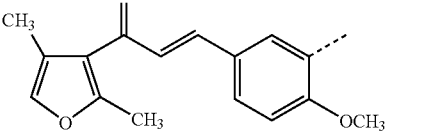 | 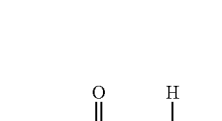 |

TABLE 1-continued

Examples of Antimitotic Agents of the Formula CHAL-LIN-COV (Formula I)

| Entry | CHAL- | -LIN- | -COV |
|---|---|---|---|
| 29 | 4-methoxyphenyl-C(=O)-C(Br)=CH-(3-methoxy,4-methoxyphenyl) | ---O-C(=O)-CH₂--- | ---S-C(=O)-CH=CH-CH₃ (trans) |
| 30 | 4-methoxyphenyl-C(=O)-C(Cl)=CH-(3-methoxy,4-methoxyphenyl) | ---O-C(=O)-CH₂--- | ---S-C(=O)-CH=CH-CH₃ (trans) |
| 31 | 4-methoxyphenyl-C(=O)-C(C₂H₅)=CH-(3-methoxy,4-methoxyphenyl) | ---O-C(=O)-CH₂--- | ---S-C(=O)-CH=CH-CH₃ (trans) |
| 32 | 6,7-dimethoxy-8-methoxy-2-(4-methoxy-3-substituted-phenyl)-4H-chromen-4-one | ---O-C(=O)-CH₂--- | ---S-C(=O)-CH=CH-CH₃ (trans) |
| 33 | 7-methoxy-8-(3-methylbut-2-enyl)-2-(4-substituted-phenyl)chroman-4-one | ---O-C(=O)-CH₂--- | ---S-C(=O)-CH=CH-CH₃ (trans) |
| 34 | 3-(3,4,5-trimethoxyphenyl)-5-(4-methoxy-3-substituted-phenyl)-1H-pyrazole | ---NH-C(=O)-CH₂--- | ---S-C(=O)-CH=CH-CH₃ (trans) |
| 35 | (3,4-dimethoxyphenyl)-C(=O)-C(CH₂-C(=O)-substituted)=CH-phenyl | ---NH-C(=O)-CH₂--- | ---S-C(=O)-CH=CH-CH₃ (trans) |

TABLE 1-continued

Examples of Antimitotic Agents of the Formula CHAL-LIN-COV (Formula I)

| Entry | CHAL- | -LIN- | -COV |
|---|---|---|---|
| 36 | (structure: chalcone with N=CH, C=O, phenyl, and 4-NO$_2$-phenyl groups) | ----O—C(=O)—CH$_2$---  (i.e., CHAL-LIN is an N—O bond) | ----S—C(=O)—C(H)=C(H)—CH$_3$ |
| 37 | (structure: 1,3-diphenyl enone with ethyl/chiral substituent) | ----N(propyl)—C(=O)—CH$_2$--- | ----S—C(=O)—C(H)=C(H)—CH$_3$ |

For purposes of the present invention, "alkyl," as used alone or in combination with other radicals (i.e., alone or in combination), refers to a straight or branched chain saturated hydrocarbon radical, which may be bonded at one end of the chain (e.g., as in a methyl group, —CH$_3$) or at two ends of the chain (e.g., as in a methylene group —CH$_2$—). Unless otherwise indicated, alkyl contains from 1 to 10 carbon atoms. "Alkenyl," alone or in combination, refers to alkyl that contains one or more carbon-to-carbon double bonds. "Alkynyl," alone or in combination, refers to alkyl that contains one or more carbon-to-carbon triple bonds.

"Cycloalkyl," alone or in combination, refers to a monocyclic, bridged monocyclic, bicyclic, tricyclic or spiro ring saturated hydrocarbon radical, which may be bonded to a parent molecule at one or more (e.g., one or two) bonding sites, wherein each ring contains from 3 to 8 carbon atoms. "Heterocycloalkyl," alone or in combination, refers to cycloalkyl having one or more carbon atoms replaced by an oxygen, nitrogen, or sulfur (including sulfoxide and sulfone) heteroatom. "Aryl," alone or in combination, refers to an unsaturated or partially unsaturated monocyclic, bridged monocyclic, bicyclic, tricyclic or spiro ring hydrocarbon radical, which may be bonded to a parent molecule at one or more (e.g., one or two) bonding sites, wherein each ring contains from 3 to 8 carbon atoms. "Heteroaryl," alone or in combination, refers to aryl having one or more carbon atoms replaced by an oxygen, nitrogen, or sulfur heteroatom. In the case of a sulfur heteroatom, "Heteroaryl" is meant to embrace the corresponding sulfoxide and sulfone derivatives. Unless otherwise indicated or apparent from the name of a specific cycloalkyl, heterocycloalkyl, aryl, or heteroaryl radical, these cyclic radicals may be bonded in the molecules described herein at any ring positions available for bonding (i.e., at any substitutable ring position).

"Aralkyl," alone or in combination, refers to alkyl in which a hydrogen atom is replaced by aryl. "Aralkenyl," alone or in combination, refers to alkenyl in which a hydrogen atom is replaced by aryl. "Aralkynyl," alone or in combination, refers to alkynyl in which a hydrogen atom is replaced by aryl. "Heteroaralkyl," "heteroaralkenyl," and "heteroaralkynyl," alone or in combination, refer to alkyl, alkenyl, and alkynyl, respectively, in which a hydrogen atom is replaced by heteroaryl.

"Hydroxy," alone or in combination, refers to the radical —OH. "Alkoxy," "alkenoxy," and "alkynyloxy," alone or in combination, refer to alkyl, alkenyl, and alkynyl, respectively, that are bonded to a molecule through an —O— linkage. For example, alkoxy, alone or in combination, refers to the radical alkyl-O—. "Cycloalkoxy," "heterocycloalkoxy," "aryloxy," and "heteroaryloxy," alone or in combination, refer to cycloalkyl, heterocycloalkyl, aryl, and heteroaryl, respectively, that are bonded to a molecule through an —O— linkage.

"Carbonyl," alone or in combination, refers to the radical —(C=O)—. "Thiocarbonyl," alone or in combination, refers to the radical —(C=S)—. "Hydroxycarbonyl," alone or in combination, refers to a radical of formic acid, —(C=O)—OH. "Alkanoyl," "alkenoyl," "alkynoyl," alone or in combination, refer to alkyl, alkenyl, and alkynyl, respectively, that are bonded to a molecule through a carbonyl linkage. For example, alkanoyl, alone or in combination, refers to the radical alkyl-(C=O)—. "Cycloalkanoyl," "heterocycloalkanoyl," "aroyl," and "heteroaroyl," alone or in combination, refer to cycloalkyl, heterocycloalkyl, aryl, and heteroaryl, respectively, that are bonded to a molecule through a carbonyl linkage.

"Carbonyloxy," alone or in combination, refers to carbonyl that is bonded to a molecule through an —O— linkage. "Alkanoyloxy," "alkenoyloxy," "alkynoyloxy," "cycloalkanoyloxy," "heterocycloalkanoyloxy," "aroyloxy," and "hetero aroyloxy," alone or in combination, refer to alkanoyl, alkenoyl, alkynoyl, cycloalkanoyl, heterocycloalkanoyl, aroyl, and heteroaroyl, respectively, that are bonded to a molecule through an —O— linkage. For example, alkanoyloxy refers to the radical alkyl-C(=O)—O—.

"Thiol," alone or in combination, refers to an —S— or —SH linkage. "Alkylthiol," "alkenylthiol," and "alkynylthiol," alone or in combination, refer to alkyl, alkenyl, and alkynyl, respectively, that are bonded to a molecule through an —S— linkage. For example, alkylthiol refers to the radical alkyl-S—. "Thiolalkyl," "thiolalkenyl," and "thiolalkynyl," alone or in combination, refer to radicals of the formula HS-alkyl-, HS-alkenyl-, and HS-alkynyl-, respectively.

"Amino," alone or in combination, embraces radicals of both primary (—NH$_2$) and secondary (—NH—) amines. Unless otherwise indicated, both primary amino and secondary amino radicals may be substituted at a hydrogen, or at both hydrogens in the case of primary amino, with one or two radicals independently selected from the group consisting of alkyl, alkenyl, alkynyl, cycloalkyl, aryl, and heteroaryl. "Alkylamino," "alkenylamino," and "alkynylamino," alone or in combination, refer to alkyl, alkenyl, and alkynyl, respectively, that are bonded to a molecule through a secondary amino (—NH—) linkage. "Amido," alone or in combination, refers to a carbonylamino radical —(C=O)—NH—. "Alkylamido," "alkenylamido," and "alkynylamido," alone or in combination, refer to alkyl, alkenyl, and alkynyl, respectively, that are bonded to a molecule through an amido linkage. For example, alkylamido refers to the radical alkyl-(C=O)—NH—. "Imino," alone or in combination, refers to the radical —(C=NH)—, wherein, unless otherwise indicated, imino may be substituted at a hydrogen with a radical as defined above with respect to amino.

"Halo," alone or in combination, refers to a halogen radical selected from —F, —Cl, —Br, and —I. "Heteroatom(s)," "heteroatomic group(s)," and "heteroatomic radical(s)" refer to atoms of oxygen, nitrogen, and sulfur, as well as groups and radicals containing these atoms.

In cases where the optional substituents (e.g., substituents, as defined for $R^3$ or $R^4$, at one or more substitutable ring positions of $R^1$ or $R^2$ in the chalcone or chalcone derivative portion of the molecule) include hydrogen, it is recognized that substitution with hydrogen is not normally considered in the art as a "substitution" or to yield a "substituted" atom (e.g., a substituted carbon atom). For purposes of the present disclosure, and in the interest of convenience, a carbon atom or heteroatom that is "substituted" or "optionally substituted" at its substitutable positions with only hydrogen (e.g., a methylene carbon atom, —$CH_2$—) is considered the same as an "unsubstituted" carbon atom or heteroatom, as conventionally defined in the art.

Compounds of the present invention can possess one or more stereocenters and are thus capable of existing in the form of pure or purified (enriched) optical isomers as well as in the form of racemic mixtures thereof. The purification of a particular optical isomer, or enrichment in one optical isomer relative to another, can be obtained according to conventional processes, for example by the formation of diastereomeric salts through treatment with an optically active acid or base. Examples of appropriate acids are tartaric, diacetyltartaric, dibenzoyltartaric, ditoluoyltartaric and camphorsulfonic acid. Examples of appropriate bases are plant-derived chiral alkaloids. The mixtures of diastereomers are then separated by crystallization, followed by liberation of the optically active bases or acids from these salts. A different process for separation of optical isomers involves the use of a chiral chromatography column chosen to maximize the separation of the enantiomers. Still another available method involves synthesis of covalent diastereomeric molecules by reaction with an optically pure acid in an activated form or an optically pure isocyanate. The synthesized diastereomers can be separated by conventional means such as chromatography, distillation, crystallization or sublimation, and then hydrolyzed to yield the enantiomerically pure compound. Various optically active compounds can likewise be obtained by utilizing optically active starting materials in the synthesis procedures described herein, as would be appreciated by those having skill in the art, with regard for the present disclosure.

It is recognized that there may be some overlap in some of the definitions of the various radicals. Specific radicals are mentioned, however, in order to emphasize their positive inclusion in the described subject matter, as not only an optional substituent. As used herein, when a particular radical, generally understood to have a single point of attachment to a core structure, such as an alkyl, alkenyl, alkynyl, or amino group, is identified in connection with a structure that must have two points of attachment in the structural core, it is understood that the named group (e.g., alkyl) refers to the parent group with a hydrogen or a site of unsaturation removed to create the second point of attachment to provide the required structure.

The term "effective amount" means the dose or effective amount to be administered to a patient and the frequency of administration to the subject which is sufficient to obtain a therapeutic effect (e.g., inhibition of the proliferation of cancer cells) as readily determined by one or ordinary skill in the art, by the use of known techniques and by observing results obtained under analogous circumstances. The dose or effective amount to be administered to a patient and the frequency of administration to the subject can be readily determined by one of ordinary skill in the art, in view of the present disclosure, by the use of known techniques and by observing results obtained under analogous circumstances. In determining the therapeutically effective amount or dose, a number of factors are considered by the attending diagnostician, including but not limited to, the potency and duration of action of the compounds used; the nature and severity of the illness to be treated as well as on the sex, age, weight, general health and individual responsiveness of the patient to be treated, and other relevant circumstances.

The phrase "therapeutically effective" indicates the capability of an agent to prevent, or reduce the severity of, the disorder or its undesirable symptoms, while avoiding adverse side effects typically associated with alternative therapies. Those skilled in the art will appreciate that dosages may also be determined with guidance from Goodman & Goldman's The Pharmacological Basis of Therapeutics, Ninth Edition (1996), Appendix II, pp. 1707-1711 and from Goodman & Goldman's The Pharmacological Basis of Therapeutics, Tenth Edition (2001), Appendix II, pp. 475-493.

Compounds of the present invention embrace not only the various stereoisomers, as discussed above, of the compounds disclosed herein, but also the various pharmaceutically acceptable isomers, tautomers, salts, esters, and prodrugs of these compounds. The term "pharmaceutically acceptable" is used herein to indicate appropriateness for use in a pharmaceutical product. Pharmaceutically acceptable salts include cationic salts, such as metallic caion and organic cation salts. Examples of pharmaceutically acceptable metallic cation salts include alkali metal salts, alkaline earth metal salts and other metal cation salts, such as the salts of aluminum, calcium, lithium, magnesium, potassium, sodium and zinc in their usual valences. Preferred organic cation salts include protonated tertiary amine salts and quaternary ammonium salts, such as the trimethylamine, diethylamine, N,N'-dibenzylethylenediamine, chloroprocaine, choline, diethanolamine, ethylenediamine, meglumine (N-methylglucamine) and procaine salts.

Examples of acids which may be employed to form pharmaceutically acceptable salts include inorganic acids and organic acids such as hydrochloric acid, hydrobromic acid, hydroiodic acid, phosphoric acid, sulfuric acid, formic acid, acetic acid, propionic acid, succinic acid, glycolic acid, gluconic acid, lactic acid, malic acid, tartaric acid, citric acid, isocitric acid, ascorbic acid, glucuronic acid, maleic acid, fumaric acid, pyruvic acid, oxalic acid, oxalacetic acid, aspartic acid, glutamic acid, benzoic acid, anthranilic acid, mesylic acid, stearic acid, salicylic acid, p-hydroxybenzoic acid, phenylacetic acid, mandelic acid, embonic (pamoic) acid, methanesulfonic acid, ethanesulfonic acid, benzenesulfonic acid, pantothenic acid, toluenesulfonic acid, 2-hydroxyethanesulfonic acid, sulfanilic acid, cyclohexylaminosulfonic acid, algenic acid, β-hydroxybutyric acid, galactaric acid, and galacturonic acid. The types of salts described above can be prepared by those skilled in the art using conventional means, from the corresponding compound of the present invention, as disclosed herein.

The term "ester" refers to a derivative of a parent compound that has similar or identical pharmacological activity and is modified to have the chemical linkage R—C(O)OR'. Thus, for example, a methyl ester derivative is obtained when R'=CH$_3$. The preparation of esters is well documented in standard chemistry textbooks. See, e.g., English et al., Principles of Organic Chemistry, 2$^{nd}$ Ed., McGraw-Hill Book Company, Inc. 245-7 (1956), describing carbonyl transfer to the oxygen of a parent molecule to yield its ester derivative.

The term "prodrug" refers to a form of the compound that has been chemically modified and becomes pharmaceutically active under physiological conditions (i.e., in the body). A prodrug may be biologically inactive at its site of action, but in this case it is degraded or modified by one or more enzymatic or other in vivo processes to the parent, bioactive form. Generally, a prodrug has a different pharmacokinetic profile than the parent compound such that, for example, it is more easily absorbed across the mucosal epithelium, it has better salt formation or solubility, and/or it has better systemic stability (e.g., an increased half-life). Those skilled in the art recognize prodrugs as chemically-modified pharmaceutical compounds that include (1) terminal ester or amide derivatives that are susceptible to being cleaved by esterases or lipases, (2) terminal peptide derivatives that may be recognized by specific or nonspecific proteases, (3) derivatives that cause accumulation at a site of action through membrane selection, and (4) forms having various combinations of these modifications. Conventional procedures for the selection and preparation of prodrug derivatives are described, for example, by H. Bundgaard, *Design of Prodrugs* (1985) and by Sinkula, A. A. and Yalkowsky, S. H.; Rationale for Design of Biologically Reversible Drug Derivatives: Prodrugs, *Journal of Pharmaceutical Sciences*, 64(2), 181-210 (1975).

The compounds of the present invention may be administered orally, parenterally, by inhalation spray, rectally, or topically in dosage unit formulations containing conventional non-toxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injections, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

While the compounds of the invention can be administered as the sole active pharmaceutical agent, they can also be used in combination with one or more anticancer agents (e.g., other antimitotic agents, alkylating agents, antimetabolites, topoisomerase inhibitors, etc.) or agents administered to reduce the side effects associated with a particular drug and/or treatment regimen. When administered as a combination, the therapeutic agents can be formulated as separate compositions which are given at the same time or different times, or the therapeutic agents can be given as a single composition.

In view of the above, it will be seen that several advantages may be achieved and other advantageous results may be obtained. Various changes could be made in the compounds and methods described above without departing from the scope of the present disclosure. It is intended that all matter contained in this application, including all theoretical mechanisms and/or modes of interaction described above, shall be interpreted as illustrative only and not limiting in any way the scope of any of the embodiments presented herein. From the foregoing description, one skilled in the art can easily ascertain the essential characteristics of this invention, and without departing from the spirit and scope thereof, can make various changes and modifications of the invention to adapt it to various usages and conditions.

Throughout this disclosure, various aspects are presented in a range format. The description of a range should be considered to have specifically disclosed all the possible subranges as well as individual numerical values within that range. For example, description of a range such as from 1 to 10 should be considered to have specifically disclosed subranges such as from 1 to 3, from 1 to 4, from 2 to 8, from 6 to 9, from 4 to 10, etc., as well as individual numbers within that range, for example, 1, 2, 3, 4, 5, etc. This applies regardless of the breadth of the range.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinency of the cited references.

The following examples are set forth as representative of the present invention. These examples are not to be construed as limiting the scope of the invention as these and other equivalent embodiments will be apparent in view of the present disclosure and appended claims.

Example 1

Preparation of 3-[3-(Crotonylsulfanylmethylcarbonyloxy)-4-methoxyphenyl]-1-(3,4,5-trimethoxyphenyl)propenone (CMAC-1) and its Activity Against Cancer Cell Growth The method of synthesis of CMAC-1 (entry 1 of Table 1) is summarized in Scheme 1.

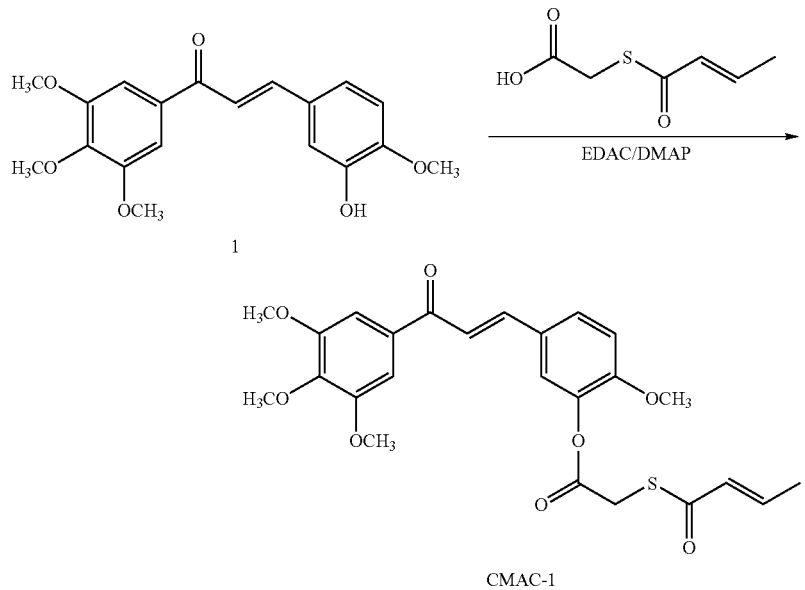

Scheme 1

CMAC-1

Chalcone CMAC-1 was synthesized by esterification of the known chalcone 1 (S. Ducki, R. Forrest, J. A. Hadfield, A. Kendall, N. J. Lawrence, A. T. McGowan, and D. Rennison, Bioorg. Med. Chem. Lett., 1998, 8, 1051-1056), itself formed from 3,4,5-trimethoxyacetophenone and 3-hydroxy-4-methoxybenzaldehyde. Chalcone 1 (0.49 g, 1.42 mmol) was dissolved in 20 mL distilled dichloromethane, and the solution was chilled to 0° C. and placed under $N_2$. To this solution were added 0.27 g (1.70 mmol, 1.2 equiv.) of but-2-enoylsulfanylacetic acid, 17 mg (0.14 mmol, 0.1 equiv.) of 4-dimethylaminopyridine (DMAP), and 0.325 g (1.70 mmol, 1.2 equiv.) of 1-(3-dimethylaminopropyl)-3-ethylcarbodiimide hydrochloride (EDAC-HCl). The reaction mixture was protected from light and allowed to stir overnight, slowly warming to room temperature. The reaction mixture was diluted with dichloromethane, sequentially washed with water, saturated aqueous sodium bicarbonate, water, 0.1 M HCl, and brine, and finally dried with sodium sulfate. The solvent was removed to yield 0.69 g of crude amber oil. Purification by rotary chromatography (silica/100% ethyl acetate, $R_f$=0.82) gave a light yellow solid, 0.558 g (81% yield). Recrystallization from 100% ethanol gave 0.40 g of light yellow solid. Mp 123-125.5° C. Anal. Calcd for $C_{25}H_{26}O_8S$: C, 61.72; H, 5.39. Found: C, 61.45; H, 5.27. $^1H$ NMR ($CDCl_3$) δ (ppm) 1.93 (dd, J=7.2, 0.9 Hz, $CHCHCH_3$), 3.87 (s, C(4'a)$OCH_3$), 3.94 (s, C(4a)$OCH_3$), 3.96 (s, C(3a)$OCH_3$ and C(5a)$OCH_3$), 4.06 (s, $CH_2S$), 6.22 (dq, J=15.3, 1.8 Hz, $CHCHCH_3$), 6.98 (d, J=9.0 Hz, C(3')H), 6.95-7.08 (m, $CHCHCH_3$), 7.27 (s, C(2)H, C(6)H), 7.33 (d, J=15.9 Hz, phenyl-COCHCH), 7.43 (d, J=2.4 Hz, C(6')H, 7.46 (dd, J=8.7, 2.1 Hz, C(2')H), 7.73 (d, J=15.9 Hz, phenyl-COCHCH). Assignments were confirmed by gCOSY, gHMBC and gHMQC experiments. $^{13}C$ NMR ($CDCl_3$) δ (ppm) 18.1 ($CHCHCH_3$), 30.7 ($COCH_2S$), 56.1 (C(4'a)$OCH_3$), 56.4 (C(3a)$OCH_3$ and C(5a)$OCH_3$), 61.0 (C(4a)$OCH_3$), 106.0 (arom C(2) and C(6)), 112.4 (arom C(3')), 120.5 (phenyl-COCHCH), 121.6 (arom C(6')), 128.1 (arom C(1')), 128.9 (arom C(2')), 129.2 ($CHCHCH_3$), 133.6 (arom C(1)), 140.1 (arom C(5')), 142.8 ($CHCHCH_3$), 143.6 (phenyl-COCHCH), 143.6 (arom C(4)), 153.1 (arom C(4')), 153.2 (arom C(3) and C(5)), 167.0 (OCO), 187.5 (SCO), 189.0 (phenyl-COCHCH).

The cancer cell growth inhibition data for the compound CMAC-1 were obtained from duplicate evaluations in the National Cancer Institute 60-cell-line cancer screen, and these data are summarized in Table 2 below:

TABLE 2

| Cancer Cell Growth Inhibition | | |
|---|---|---|
| | $GI_{50}/M$ | $GI_{50}/M$ |
| Leukemia | | |
| CCRF-CEM | $7.16 \times 10^{-8}$ | $8.60 \times 10^{-8}$ |
| HL60-(TB) | $<1.00 \times 10^{-8}$ | $<1.00 \times 10^{-8}$ |
| K562 | $<1.00 \times 10^{-8}$ | $<1.00 \times 10^{-8}$ |
| MOLT-4 | $4.89 \times 10^{-7}$ | $1.77 \times 10^{-7}$ |
| RPMI-8226 | $<1.00 \times 10^{-8}$ | $<1.00 \times 10^{-8}$ |
| SR | $<1.00 \times 10^{-8}$ | $<1.00 \times 10^{-8}$ |
| NSCLC | | |
| A549/ATCC | $7.89 \times 10^{-7}$ | $2.49 \times 10^{-7}$ |
| EKVX | $2.09 \times 10^{-6}$ | $1.70 \times 10^{-6}$ |
| HOP-62 | $1.23 \times 10^{-6}$ | $1.00 \times 10^{-6}$ |
| HOP-92 | $6.15 \times 10^{-7}$ | $4.67 \times 10^{-8}$ |
| NCI-H226 | $1.72 \times 10^{-5}$ | $1.12 \times 10^{-5}$ |
| NCI-H23 | $2.39 \times 10^{-7}$ | $3.54 \times 10^{-5}$ |

TABLE 2-continued

Cancer Cell Growth Inhibition

| | $GI_{50}/M$ | $GI_{50}/M$ |
|---|---|---|
| NCI-H322M | $8.51 \times 10^{-8}$ | $7.03 \times 10^{-8}$ |
| NCI-H460 | $5.24 \times 10^{-8}$ | $3.35 \times 10^{-8}$ |
| NCI-H522 | $2.24 \times 10^{-8}$ | $1.58 \times 10^{-8}$ |
| Colon | | |
| COLO 205 | $4.22 \times 10^{-6}$ | $1.00 \times 10^{-5}$ |
| HCC-2998 | $1.33 \times 10^{-6}$ | $1.41 \times 10^{-7}$ |
| HCT-116 | $3.92 \times 10^{-8}$ | $1.92 \times 10^{-8}$ |
| HCT-15 | $<1.00 \times 10^{-8}$ | $<1.00 \times 10^{-8}$ |
| HT29 | $2.87 \times 10^{-6}$ | $1.68 \times 10^{-6}$ |
| KM12 | $8.97 \times 10^{-8}$ | $4.39 \times 10^{-8}$ |
| SW-620 | $<1.00 \times 10^{-8}$ | $<1.00 \times 10^{-8}$ |
| CNS | | |
| SF-268 | $8.11 \times 10^{-8}$ | $6.38 \times 10^{-8}$ |
| SF-295 | $2.15 \times 10^{-7}$ | $2.31 \times 10^{-7}$ |
| SF-539 | $1.64 \times 10^{-8}$ | $<1.00 \times 10^{-8}$ |
| SNB-19 | $1.88 \times 10^{-5}$ | $1.22 \times 10^{-8}$ |
| SNB-75 | $1.65 \times 10^{-8}$ | $<1.00 \times 10^{-8}$ |
| U251 | $4.27 \times 10^{-8}$ | $5.21 \times 10^{-8}$ |
| Melanoma | | |
| LOX IMVI | $1.85 \times 10^{-8}$ | $6.12 \times 10^{-8}$ |
| MALMI-3M | $7.42 \times 10^{-8}$ | $4.47 \times 10^{-8}$ |
| M14 | $6.23 \times 10^{-8}$ | — |
| SK-MEL-2 | $1.15 \times 10^{-5}$ | $6.76 \times 10^{-8}$ |
| SK-MEL-28 | $2.19 \times 10^{-6}$ | $7.89 \times 10^{-8}$ |
| SK-MEL-5 | $2.91 \times 10^{-7}$ | $2.18 \times 10^{-8}$ |
| UACC-257 | $3.58 \times 10^{-6}$ | $4.14 \times 10^{-6}$ |
| UACC-62 | $5.22 \times 10^{-7}$ | $1.38 \times 10^{-6}$ |
| Ovarian | | |
| IGROV1 | $7.60 \times 10^{-6}$ | $4.31 \times 10^{-8}$ |
| OVCAR-3 | $1.16 \times 10^{-8}$ | $<1.00 \times 10^{-8}$ |
| OVCAR-4 | $1.05 \times 10^{-6}$ | $4.60 \times 10^{-7}$ |
| OVCAR-5 | $7.02 \times 10^{-8}$ | $3.13 \times 10^{-8}$ |
| OVCAR-8 | $4.39 \times 10^{-8}$ | $4.71 \times 10^{-8}$ |
| SKOV-3 | $1.34 \times 10^{-5}$ | $5.60 \times 10^{-8}$ |
| Renal | | |
| 786-0 | $2.20 \times 10^{-7}$ | $6.37 \times 10^{-8}$ |
| A498 | $1.20 \times 10^{-5}$ | $1.81 \times 10^{-6}$ |
| ACHN | $6.66 \times 10^{-8}$ | $2.39 \times 10^{-6}$ |
| CAKI-1 | $2.33 \times 10^{-6}$ | $8.38 \times 10^{-7}$ |
| RXF-393 | $1.47 \times 10^{-7}$ | $1.95 \times 10^{-8}$ |
| SN12C | $1.22 \times 10^{-6}$ | $7.91 \times 10^{-6}$ |
| TK-10 | $3.06 \times 10^{-6}$ | $1.19 \times 10^{-6}$ |
| UO-31 | $1.76 \times 10^{-6}$ | $2.44 \times 10^{-8}$ |
| Prostate | | |
| PC-3 | $3.37 \times 10^{-6}$ | $2.76 \times 10^{-7}$ |
| DU-145 | $3.19 \times 10^{-8}$ | $1.32 \times 10^{-8}$ |
| Breast | | |
| MCF7 | $2.85 \times 10^{-8}$ | $3.00 \times 10^{-8}$ |
| NCI/ADR-RES | $2.62 \times 10^{-8}$ | $3.22 \times 10^{-8}$ |
| MDA-MB-231/ | $2.40 \times 10^{-7}$ | $5.85 \times 10^{-8}$ |
| HS 578T | $4.04 \times 10^{-8}$ | $2.06 \times 10^{-8}$ |
| MDA-MB-435 | $<1.00 \times 10^{-8}$ | $<1.00 \times 10^{-8}$ |
| BT-549 | $4.38 \times 10^{-8}$ | $<1.00 \times 10^{-8}$ |
| T-47D | $3.07 \times 10^{-6}$ | $1.14 \times 10^{-5}$ |

Testing in the NCI 60-cell-line panel showed $GI_{50}$ values (Table 2) of <10 nanomolar for leukemia (HL-60, K-562, RPMI-8226, SR), colon (HCT-15, SW-620), and breast cancer cells (MDA-MB-435), and <50 nanomolar for individual cell lines of non-small-cell lung cancer (NSCLC), central nervous system (CNS) cancer, ovarian cancer, and prostate cancer. Melanoma responded with $GI_{50}$ values of <75 nanomolar, and renal cancer with <150 nanomolar. These results indicated a very high degree of anticancer activity of CMAC-1 against a wide range of cancers.

Cell growth inhibition studies whose results are reported above were carried out at the National Cancer Institute essentially as follows. Cells grown in RPMI 1640 medium containing 5% fetal bovine serum and 2 mM L-glutamine were inoculated into 96-well microtiter plates, which were incubated for 24 hours prior to addition of CMAC-1 at five concentrations. After 48 hours, cold trichloroacetic acid was added, and the plates were washed and air dried. The cells were stained with sulforhodamine B (SRB), and the absorbance was read on an automated plate reader at a wavelength of 515 nm. The percentage growth was calculated at each of the drug concentrations. The growth inhibition of 50% ($GI_{50}$) was then calculated. The $GI_{50}$ is the drug concentration resulting in a 50% reduction in the net protein increase (as measured by SRB staining) in control cells during the drug incubation.

CMAC-1 was found to inhibit the growth of human pancreatic cancer cells in culture. The concentration required for 50% growth inhibition of MIA PaCa-2 cells ($GI_{50}$) was 16 nanomolar. This is an exceedingly low concentration and indicates a high activity for CMAC-1.

Growth inhibition assays for determination of $GI_{50}$ values in pancreatic cancer cell lines were typically carried out essentially as follows. Compounds were individually tested at various concentrations against cancer cells grown in cell culture. The cell viability was determined by use of a standard assay that employs 3-(4,5-dimethylthiazol-2-yl)-5-(3-carboxymethoxyphenyl)-2-(4-sulfophenyl)-2H-tetrazolium, inner salt (MTS), and an electron coupling reagent, phenazine methosulfate (PMS). Absorbance at 490 nm ($A_{490}$) was measured, and survival curves were obtained by comparison of $A_{490}$ from treated cells with $A_{490}$ from untreated cells (control). $GI_{50}$ values were calculated from nonlinear curve fitting.

Example 2

Preparation of 3-[5-(Crotonylsulfanylmethylcarbonyloxymethyl)-2-furyl]-1-(3,4,5-trimethoxyphenyl) propenone (CMAF-1) and its Activity Against Cancer Cell Growth The method of synthesis of CMAF-1 (entry 11 of Table 1) is summarized in Scheme 2.

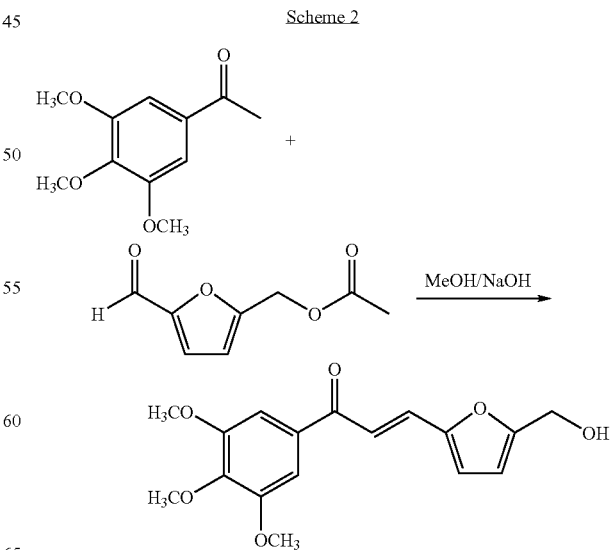

-continued

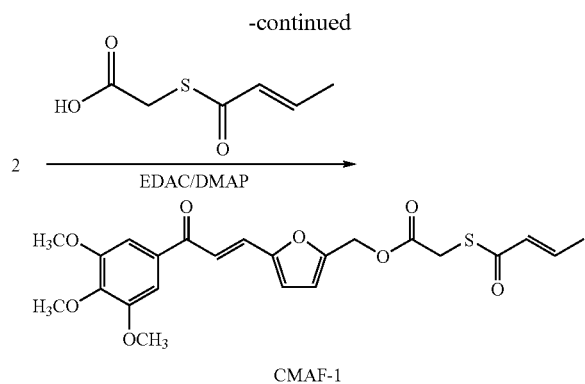

CMAF-1

Preparation of Chalcone 2 was accomplished by Claisen-Schmidt condensation, as follows. In 5 mL methanol were dissolved 1.43 g (6.8 mmol) of 3,4,5-trimethoxyacetophenone and 1.14 g (6.8 mmol) of 5-acetoxymethyl-2-furaldehyde. After addition of 0.37 g crushed NaOH, the reaction mixture was stirred overnight to yield a dark solid material. This was taken up in methanol, collected by filtration, and washed with ice water to yield a mustard yellow powder (1.35 g, 55%). The material was recrystallized from $H_2O$-methanol. Mp 86-88° C. $^1$H NMR (CDCl$_3$) δ (ppm) 2.2 (br s, 1H), 3.93 (s, 3H), 3.95 (s, 6H), 4.70 (s, 2H), 6.42 (d, J=3.3 Hz, 1H), 6.67 (d, J=3.3 Hz, 1H), 7.28 (s, 2H), 7.38 (d, J=15.3 Hz, 1H), 7.56 (d, J=15.6 Hz, 1H).

Esterification of chalcone 2 to produce CMAF-1 was carried out as follows. Chalcone 2 (0.19 g, 0.60 mmol) was dissolved in 20 mL distilled dichloromethane, and the solution was chilled to 0° C. and placed under $N_2$. After addition of 0.12 g (0.72 mmol, 1.2 equiv.) of but-2-enoylsulfanylacetic acid, 15 mg (0.12 mmol, 0.2 equiv.) of 4-dimethylaminopyridine (DMAP), and 0.171 g (0.89 mmol, 1.5 equiv.) of 1-(3-dimethylaminopropyl)-3-ethylcarbodiimide hydrochloride (EDAC-HCl, the reaction mixture was protected from light and allowed to stir overnight, slowly warming to room temperature. The reaction mixture was diluted with chloroform, sequentially washed with water, dilute sodium bicarbonate, 0.1 M HCl, and brine, and dried with sodium sulfate. The solvent was removed to yield 0.26 g (94%) of brown solid. This was purified by rotary chromatography (silica/ethyl acetate-hexane (1:1, v/v), $R_f$=0.56) to give a yellow oil. Anal. Calcd for $C_{23}H_{24}O_8S$: C, 59.99; H, 5.25. Found: C, 59.95; H, 5.02. $^1$H NMR (CDCl$_3$) δ (ppm) 1.81 (dd, J=6.5, 1.5 Hz, CHCHCH$_3$), 3.73 (s, CH$_2$S), 3.86 (s, OCH$_3$), 3.89 (s, 6H, OCH$_3$), 5.11 (s, CH$_2$O), 6.08 (dd, J=15.3, 1.8 Hz, CHCHCH$_3$), 6.47 (d, J=3.3 Hz, furan C(4)H), 6.61 (d, J=3.3 Hz, furan C(3)H), 6.88 (dq, J=15.3, 7.2 Hz, CHCHCH$_3$), 7.23 (s, phenyl C(2)H and C(6)H), 7.35 (d, J=15.6 Hz, phenyl-COCHCH), 7.49 (d, J=15.3, phenyl-COCHCH). $^{13}$C NMR (CDCl$_3$) δ (ppm) 18.1 (CHCHCH$_3$), 31.5 (CH$_2$S), (56.4 C(3) OCH$_3$) and C(5)OCH$_3$), 59.1 (furan(C-2)-CH$_2$O), 61.0 (C(4) OCH$_3$), 106.0 (phenyl C(2) and C(6)), 113.7 (furan C(3)), 116.9 (furan C(4)), 119.5 (phenyl-COCHCH), 129.1 (CH$_3$CHCH), 130.1 (phenyl-COCHCH), 133.3 (phenyl C(1)), 142.6 (phenyl C(4)), 142.7 (CH$_3$CHCH), 151.4 (furan C(2)), 152.1 (furan C(5)), 153.0 (phenyl C(3) and C(5)), 168.5 (OCOCH$_2$S), 187.5 (COCHCHCH$_3$), 188.4 (phenyl-COCHCH).

CMAF-1 was found to inhibit human pancreatic cancer cell (MIA PaCa-2) growth in culture with an GI$_{50}$ of 17 micromolar by the method described in EXAMPLE 1.

The findings from the synthetic procedures and testing protocol described in EXAMPLES 1 and 2 (as well as EXAMPLE 3 below) indicate that antimitotic agents of the present invention are active against cancer cell growth. Representative compounds will exhibit GI$_{50}$ values of less than about 50 micromolar (e.g., from about 1 to about 50 micromolar), less than about 20 micromolar (e.g., from about 1 to about 20 micromolar), less than about 10 micromolar (e.g., from about 1 to about 10 micromolar), less than about 1 micromolar (e.g., from about 1 nanomolar to about 1 micromolar), less than about 100 nanomolar (e.g., from about 1 to about 100 nanomolar), less than about 50 nanomolar (e.g., from about 1 to about 50 nanomolar), less than about 20 nanomolar (e.g., from about 1 to about 20 nanomolar), and in some cases even less that about 10 nanomolar (e.g., from about 1 to about 10 nanomolar).

Example 3

Activity Against Cancer Cell Growth of 3-[3-(2-Chloroacryloyloxy)-4-methoxyphenyl]-1-(3,4,5-trimethoxyphenyl)propenone 3-[3-(2-Chloroacryloyloxy)-4-methoxyphenyl]-1-(3,4,5-trimethoxyphenyl)propenone (entry 6 of Table 1). Mp 120-121° C. Anal. (%) Calcd. for $C_{21}H_{21}ClO_7$: C, 59.93; H, 5.03. Found: C, 60.08; H, 5.04. $^1$H NMR (300 MHz, CDCl$_3$) δ (ppm) 3.86 (s, C(4'a)OCH$_3$), 3.91 (s, C(4a)OCH$_3$), 3.93 (s, C(3a)OCH$_3$ and C(5a)OCH$_3$), 6.20 (d, J=2.0 Hz, CClCHH), 6.76 (d, J=3.0 Hz, CClCHH), 7.00 (d, J=8.1 Hz, C(3')H), 7.24 (s, C(2)H, C(6)H), 7.32 (d, J=15.6 Hz, O=CCHCH), 7.43 (d, J=2.1 Hz, C(6')H), 7.50 (dd, J=8.4, 2.1 Hz, C(2')H), 7.73 (d, J=15.3 Hz, O=CCHCH). $^{13}$C NMR (100 MHz, CDCl$_3$) δ (ppm) 56.2 (C(4'a)OCH$_3$), 56.5 (C(3a)OCH$_3$ and C(5a) OCH$_3$), 61.0 (C(4a)OCH$_3$), 106.0 (arom C(2), C(6)), 112.5 (arom C(3')), 120.5 (O=CCHCH), 121.5 (arom C(6')), 127.7 (CCl=CH$_2$), 128.1 (arom C(1')), 129.1 (arom C(2')), 130.6 (CCl=CH$_2$), 133.6 (arom C(1)), 139.8 (arom C(5')), 142.1 (arom C(4)), 143.3 (O=CCHCH), 152.8 (arom C(4')), 153.1 (arom C(3) and C(5)), 159.9 (OCO), 188.8 (O=CCHCH).

Cell culture data for 3-[3-(2-chloroacryloyloxy)-4-methoxyphenyl]-1-(3,4,5-trimethoxyphenyl)propenone (entry 6 of Table 1) were determined to be as follows: Mia PaCa-2 (pancreatic) cancer cells: 50% growth inhibition (GI$_{50}$)=56 nanomolar; BxPC-3 (pancreatic) cancer cells: 4.5 micromolar.

Example 4

Reaction of CMAC-1 with Thiol Nucleophile

To probe the reactivity of the α,β-unsaturated thiol ester CMAC-1 with a thiol nucleophile like that of tubulin, an NMR study was carried out. CMAC-1 (7.2 mg/0.7 mL CDCl$_3$) was treated with one equivalent of N-acetylcysteamine (the thiol nucleophile) as a tubulin model compound. There was no observable change in the NMR spectrum, as the free thiol group (R—S—H) is much less nucleophilic than the thiolate (i.e., the deprotonated form, R—S$^-$). To deprotonate the neutral thiol and convert it into the thiolate, 0.1 equivalent of a base (DBN, 1,5-diazabicyclo[4.3.0]non-5-ene) was added. Within 10 minutes of addition of DBN, 89% of CMAC-1 had been converted to the product of nucleophilic addition, shown below in Scheme 3, as evidenced by loss of the thiol ester vinyl proton resonances (S—C(=O)—CH=CH—CH$_3$) and an upfield shift of the terminal CH$_3$ signal from δ 1.8 to 1.3 ppm. Two minor products were also observed.

Scheme 3

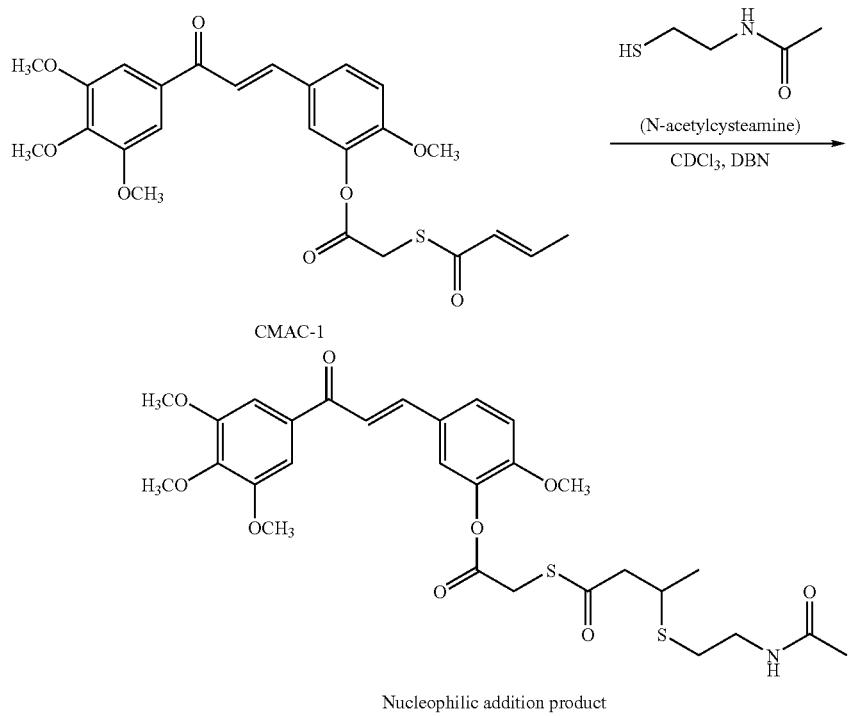

Nucleophilic addition product

What is claimed is:
1. A compound represented by the formula

CHAL-LIN-COV, wherein
(A) CHAL has the formula

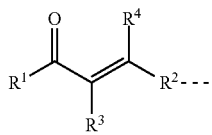

wherein $R^1$ and $R^2$ represent radicals independently selected from the group consisting of cycloalkyl,
wherein cycloalkyl, heterocycloalkyl, aryl, or heteroaryl are optionally independently substituted at one or more substitutable ring positions with (A) a radical as defined for $R^3$ or $R^4$; or (B) =O, =S, =NH, =NOH, or =NNH$_2$, wherein =NH, =NOH, or =NNH$_2$, optionally have one or more hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;
$R^3$ and $R^4$ are independently hydrogen radicals or saturated or partially unsaturated straight chain, branched, or cyclic hydrocarbon radicals having from 1 to about 20 carbon atoms, wherein
(1) one or more carbon atoms having one or more bound hydrogen atoms (i.e., hydrogen radicals) are optionally substituted with a monovalent radical independently selected from alkyl, alkenyl, alkynyl, cycloalkyl, heterocycloalkyl, aryl, heteroaryl —OH, —SH, —SOH, —SO$_2$H, —SO$_3$H, —NH$_2$, —NO$_2$, —CO$_2$H, —CONH$_2$, —CN, —F, —Cl, —Br, and —I, wherein the monovalent heteroatomic radicals —OH, —SH, —SOH, —SO$_2$H, —SO$_3$H, —NH$_2$, —CO$_2$H, —CONH$_2$ optionally have one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;
(2) one or more carbon atoms having two or more bound hydrogen atoms are optionally substituted with a divalent radical independently selected from =O, =S, =NH, =NOH, and =NNH$_2$, wherein the divalent heteroatomic radicals =NH, =NOH, and =NNH$_2$ optionally have one or more bound hydrogen atoms (i.e., hydrogen radicals) independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and
(3) one or more methylene carbon atoms (—CH$_2$—) are optionally replaced by a divalent radical independently selected from alkyl, alkenyl, alkynyl, cycloalkyl, heterocycloalkyl, aryl, heteroaryl, —O—, —S—, —NH—, —OCO—, —CO$_2$—, —CONH—, —OCONH—, and —CO$_2$NH—, wherein the divalent heteroatomic radicals —NH—, —CONH—, —OCONH—, and —CO$_2$NH— optionally have one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I, or R³ and R⁴ are independently selected from the group consisting of —OH, —SH, —SOH, —SO₂H, —SO₃H, —NH₂, —NO₂, —CO₂H, —CONH₂, —CN, —F, —Cl, —Br, and —I, wherein —OH, —SH, —SOH, —SO₂H, —SO₃H, —NH₂, —CO₂H, or —CONH₂ optionally has one or more hydrogen radicals independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I; and (B) LIN is a bond or a saturated or partially unsaturated straight chain, branched, or cyclic hydrocarbon radical having from 1 to about 40 carbon atoms, and (C) COV is selected from the group consisting of -oxycarbonylalkyl, -oxycarbonylalkenyl, -oxycarbonylalkynyl, -(secondary)aminocarbonylalkyl, -(secondary)aminocarbonylalkenyl, -(secondary)aminocarbonylalkynyl, -(thiol)carbonylalkyl, -(thiol)carbonylalkenyl, -(thiol)carbonylalkynyl, -oxy(thiocarbonyl)alkyl, -oxy(thiocarbonyl)alkenyl, -oxy(thiocarbonyl)alkynyl, -(secondary)amino(thiocarbonyl)alkyl, -(secondary)amino(thiocarbonyl)alkenyl, -(secondary)amino(thiocarbonyl)alkynyl, -(thiol)(thiocarbonyl)alkyl, -(thiol)(thiocarbonyl)alkenyl, -(thiol)(thiocarbonyl)alkynyl, -oxyiminoalkyl, -oxyiminoalkenyl, -oxyiminoalkynyl, -(secondary)aminoiminoalkyl, -(secondary)aminoiminoalkenyl, -(secondary)aminoiminoalkynyl, -(thiol)iminoalkyl, -(thiol)iminoalkenyl, -(thiol)iminoalkynyl, wherein alkyl, alkenyl, and alkynyl have from 0 to about 20 carbon atoms, wherein, in any of (I) R³ or R⁴ of CHAL, (II) a carbon atom of LIN, or (III) alkyl, alkenyl, or alkynyl of COV, (1) one or more carbon atoms having one or more bound hydrogen atoms are optionally independently substituted with alkyl, alkenyl, alkynyl, cycloalkyl, heterocycloalkyl, aryl, heteroaryl —OH, —SH, —SOH, —SO₂H, —SO₃H, —NH₂, —NO₂, —CO₂H, —CONH₂, —CN, —F, —Cl, —Br, or —I, wherein —OH, —SH, —SOH, —SO₂H, —SO₃H, —NH₂, —CO₂H, or —CONH₂ optionally has one or more bound hydrogen atoms independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I;

(2) one or more carbon atoms having two or more bound hydrogen atoms are optionally independently substituted with =O, =S, =NH, =NOH, or =NNH₂, wherein =NH, =NOH, or =NNH₂ optionally has one or more bound hydrogen atoms independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I; and (3) one or more methylene carbon atoms (—CH₂—) are optionally replaced by alkyl, alkenyl, alkynyl, cycloalkyl, heterocycloalkyl, aryl, heteroaryl, —O—, —S—, —NH—, —OCO—, —CO₂—, —CONH—, —OCONH—, or —CO₂NH—, wherein —NH—, —CONH—, —OCONH—, or —CO₂NH— optionally has one or more hydrogen radicals independently replaced by alkyl, alkenyl, alkynyl, cycloalkyl, heterocycloalkyl, aryl, heteroaryl, —OH, —SH, —SOH, —SO₂H, —SO₃H, —NH₂, —NO₂, —CO₂H, —CONH₂, —CN, —F, —Cl, —Br, or —I, or a pharmaceutically acceptable salt or ester thereof.

2. The compound of claim 1, wherein
R³ and R⁴ are hydrogen or R³, R⁴, and the optional substituents of R¹ and R² are independently alkyl, hydroxy, or alkoxy.

3. The compound of claim 1, wherein CHAL is selected from the group consisting of

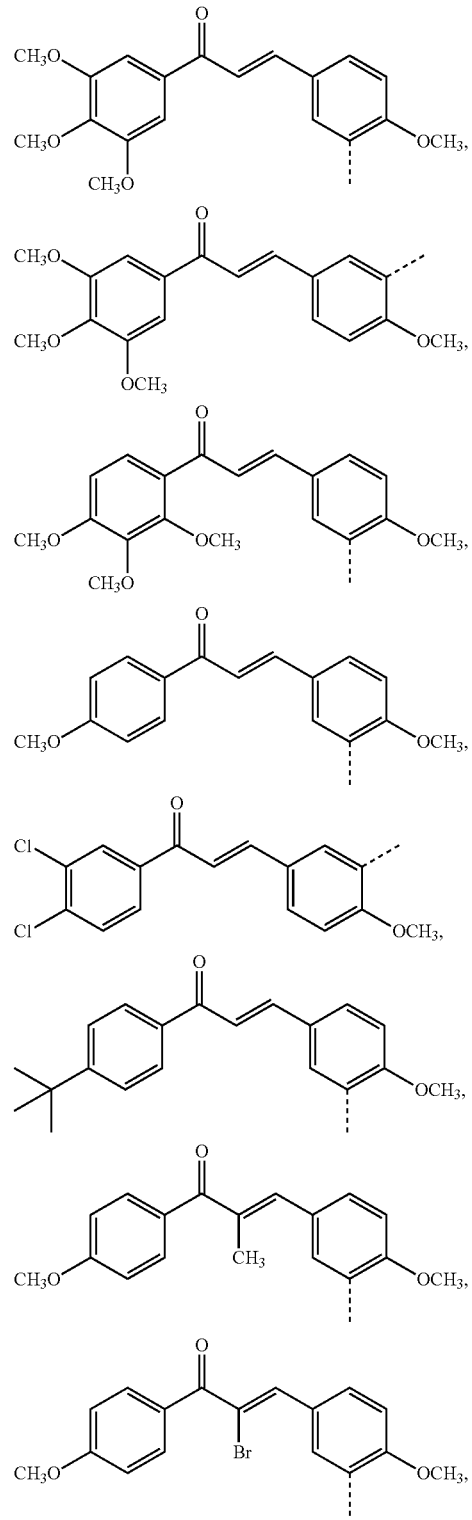

-continued

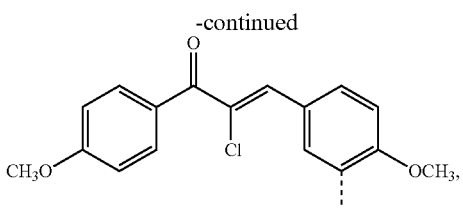

and

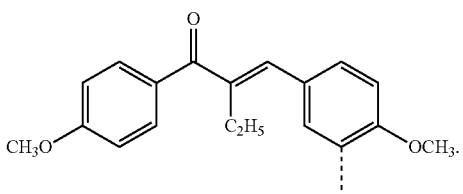

4. The compound of claim 1, wherein LIN is a bond or is selected from the group consisting of -alkoxycarbonylalkyl-, -alkenoxycarbonylalkyl-, -alkynyloxycarbonylalkyl-, -alkoxycarbonylalkenyl-, -alkenoxycarbonylalkenyl-, -alkynyloxycarbonylalkenyl-, -alkoxycarbonylalkynyl-, -alkenoxycarbonylalkynyl-, -alkynyloxycarbonylalkynyl-, -alkylaminocarbonylalkyl-, -alkenylaminocarbonylalkyl-, -alkynylaminocarbonylalkyl-, -alkylaminocarbonylalkenyl-, -alkenylaminocarbonylalkenyl-, -alkynylaminocarbonylalkenyl-, -alkylaminocarbonylalkynyl-, -alkenylaminocarbonylalkynyl-, -alkynylaminocarbonylalkynyl-, -(alkylthiol)carbonylalkyl-, -(alkenylthiol)carbonylalkyl-, -(alkynylthiol)carbonylalkyl-, -(alkylthiol)carbonylalkenyl-, -(alkenylthiol)carbonylalkenyl-, -(alkynylthiol)carbonylalkenyl-, -(alkylthiol)carbonylalkynyl-, -(alkenylthiol)carbonylalkynyl-, -(alkynylthiol)carbonylalkynyl-, -alkoxyiminoalkyl-, -alkenoxyiminoalkyl-, -alkynoxyiminoalkyl-, -alkoxyiminoalkenyl-, -alkenoxyiminoalkenyl-, -alkynoxyiminoalkenyl-, -alkynoxyiminoalkynyl-, -alkenoxyiminoalkynyl-, -alkynoxyiminoalkynyl-, -alkylaminoiminoalkyl-, -alkenylaminoiminoalkyl-, -alkynylaminoiminoalkyl-, -alkylaminoiminoalkenyl-, -alkenylaminoiminoalkenyl-, -alkynylaminoiminoalkenyl-, -alkylaminoiminoalkynyl-, -alkenylaminoiminoalkynyl-, -alkynylaminoiminoalkynyl-, -alkylthioliminoalkyl-, -alkenylthioliminoalkyl-, -alkynylthioliminoalkyl-, -alkylthioliminoalkenyl-, -alkenylthioliminoalkenyl-, -alkynylthioliminoalkenyl-, -alkylthioliminoalkynyl-, -alkenylthioliminoalkynyl-, -alkynylthioliminoalkynyl-, -alkoxy(thiocarbonyl)alkyl-, -alkenoxy(thiocarbonyl)alkyl-, -alkynoxy(thiocarbonyl)alkyl-, -alkynoxy(thiocarbonyl)alkenyl-, -alkoxy(thiocarbonyl)alkynyl-, -alkenoxy(thiocarbonyl)alkynyl-, -alkynoxy(thiocarbonyl)alkynyl-, -alkylamino(thiocarbonyl)alkyl-, -alkenylamino(thiocarbonyl)alkyl-, -alkynylamino(thiocarbonyl)alkyl-, -alkylamino(thiocarbonyl)alkenyl-, -alkenylamino(thiocarbonyl)alkenyl-, -alkynylamino(thiocarbonyl)alkenyl-, -alkylamino(thiocarbonyl)alkynyl-, -alkenylamino(thiocarbonyl)alkynyl-, -alkynylamino(thiocarbonyl)alkynyl-, -alkylthiol(thiocarbonyl)alkyl-, -alkenylthiol(thiocarbonyl)alkyl-, -alkynylthiol(thiocarbonyl)alkyl-, -alkylthiol(thiocarbonyl)alkenyl-, -alkenylthiol(thiocarbonyl)alkenyl-, -alkynylthiol(thiocarbonyl)alkenyl-, -alkylthiol(thiocarbonyl)alkynyl-, -alkenylthiol(thiocarbonyl)alkynyl-, and -alkynylthiol(thiocarbonyl)alkynyl-, wherein, in LIN, alkyl, alkenyl, alkynyl, and the alkyl, alkenyl, and alkynyl portions of alkoxy, alkenoxy, alkynoxy, alkylamino, alkenylamino, alkynylamino, alkylthiol, alkenylthiol, and alkynylthiol independently have from 0 to about 20 carbon atoms, wherein (i) one or more carbon atoms having one or more bound hydrogen atoms are optionally independently substituted with alkyl having 1-3 carbon atoms, alkenyl having 1-3 carbon atoms, alkynyl having 1-3 carbon atoms, hydroxy, or alkyloxy having 1-3 alkyl carbon atoms;

(ii) one or more carbon atoms having two or more bound hydrogen atoms are optionally independently substituted with =O, =S, or =NH; and (iii) one or more methylene carbon atoms (—CH$_2$—) are optionally independently replaced by —O—, —NH—, or —S—.

5. The compound of claim 4, wherein LIN is a bond.

6. The compound of claim 4, wherein LIN is selected from the group consisting of -oxycarbonylalkyl-, -(secondary)aminocarbonylalkyl-, and -(thiol)carbonylalkyl-, -oxy(thiocarbonyl)alkyl-, -(secondary)amino(thiocarbonyl)alkyl-, -(thiol)(thiocarbonyl)alkyl-, -oxyiminoalkyl-, -(secondary)aminoiminoalkyl-, and -(thiol)iminoalkyl-, wherein alkyl has from 0 to about 20 carbon atoms, wherein (i) one or more carbon atoms having one or more bound hydrogen atoms are optionally independently substituted with alkyl having 1-3 carbon atoms, alkenyl having 1-3 carbon atoms, alkynyl having 1-3 carbon atoms, hydroxy, or alkyloxy having 1-3 alkyl carbon atoms;

(ii) one or more carbon atoms having two or more bound hydrogen atoms are optionally independently substituted with =O, =S, or =NH; and (iii) one or more methylene carbon atoms (—CH$_2$—) are optionally independently replaced by —O—, —NH—, or —S—.

7. The compound of claim 6, wherein LIN is -oxycarbonylalkyl-.

8. The compound of claim 1, wherein LIN is a bond or is selected from the group consisting of

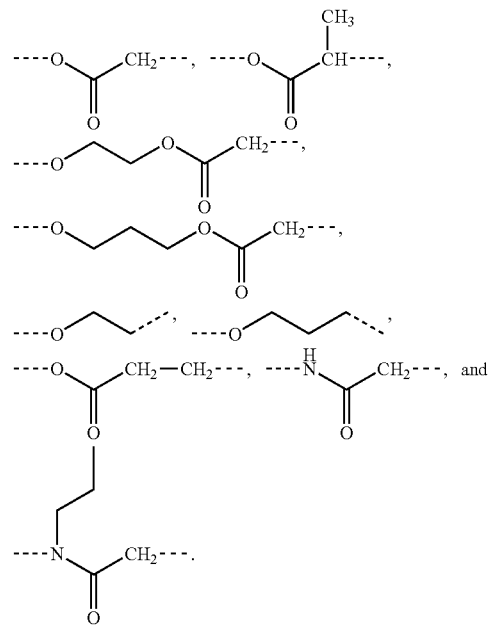

9. The compound of claim 1, wherein COV is selected from the group consisting of -oxycarbonylalkenyl, -(secondary)aminocarbonylalkenyl, -(thiol)carbonylalkenyl, -oxy(thiocarbonyl)alkenyl, -(secondary)amino(thiocarbonyl)alkenyl, -(secondary)amino(thiocarbonyl)alkenyl, -(thiol)(thiocarbonyl)alkenyl, -oxyiminoalkenyl, -(secondary)aminoiminoalkenyl, and -(thiol)iminoalkenyl, wherein alkenyl has from 0 to about 10 carbon atoms, wherein (1) one or more carbon atoms having one or more bound hydrogen atoms are optionally independently substituted with alkyl, alkenyl, alkynyl, cycloalkyl, heterocycloalkyl, aryl, heteroaryl —OH, —SH, —SOH, —SO$_2$H, —SO$_3$H, —NH$_2$, —NO$_2$, —CO$_2$H, —CONH$_2$, —CN, —F, —Cl, —Br, or —I, wherein —OH, —SH, —SOH, —SO$_2$H, —SO$_3$H, —NH$_2$, —CO$_2$H, or —CONH$_2$ optionally has one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;

(2) one or more carbon atoms having two or more bound hydrogen atoms are optionally independently substituted with =O, =S, =NH, =NOH, or =NNH$_2$, wherein =NH, =NOH, or =NNH$_2$ optionally has one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by alkyl, alkenyl, alkynyl, cycloalkyl, heterocycloalkyl, aryl, heteroaryl, —O—, —S—, —NH—, —OCO—, —CO$_2$—, —CONH—, —OCONH—, or —CO$_2$NH—, wherein —NH—, —CONH—, —OCONH—, or —CO$_2$NH— optionally has one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

10. The compound of claim 9, wherein COV is selected from the group consisting of

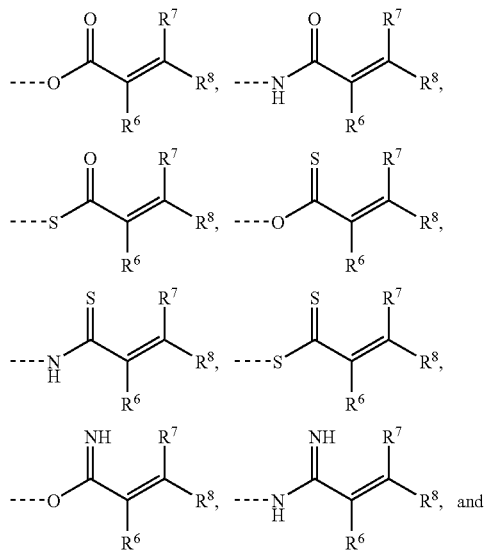

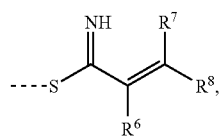

wherein $R^6$, $R^7$, and $R^8$ independently represent radicals as defined with respect to $R^3$ and $R^4$ in CHAL.

11. The compound of claim 9, wherein COV is selected from the group consisting of -oxycarbonylalkyl, -oxycarbonylalkenyl, -(secondary)aminocarbonylalkenyl, and -(thiol)carbonylalkenyl, wherein alkyl or alkenyl independently have from 0 to about 10 carbon atoms, wherein (1) one or more carbon atoms having one or more bound hydrogen atoms are optionally independently substituted with alkyl, alkenyl, alkynyl, cycloalkyl, heterocycloalkyl, aryl, heteroaryl —OH, —SH, —SOH, —SO$_2$H, —SO$_3$H, —NH$_2$, —NO$_2$, —CO$_2$H, —CONH$_2$, —CN, —F, —Cl, —Br, or —I, wherein —OH, —SH, —SOH, —SO$_2$H, —SO$_3$H, —NH$_2$, —CO$_2$H, or —CONH$_2$ optionally has one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I;

(2) one or more carbon atoms having two or more bound hydrogen atoms are optionally independently substituted with =O, =S, =NH, =NOH, or =NNH$_2$, wherein =NH, =NOH, or =NNH$_2$ optionally has one or more bound hydrogen atoms independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I; and (3) one or more methylene carbon atoms (—CH$_2$—) are optionally replaced by alkyl, alkenyl, alkynyl, cycloalkyl, heterocycloalkyl, aryl, heteroaryl, —O—, —S—, —NH—, —OCO—, —CO$_2$—, —CONH—, —OCONH—, or —CO$_2$NH—, wherein —NH—, —CONH—, —OCONH—, or —CO$_2$NH— optionally has one or more hydrogen radicals independently replaced by alkyl, alkenyl, alkynyl, cycloalkyl, heterocycloalkyl, aryl, heteroaryl, —OH, —SH, —SOH, —SO$_2$H, —SO$_3$H, —NH$_2$, —NO$_2$, —CO$_2$H, —CONH$_2$, —CN, —F, —Cl, —Br, or —I.

12. The compound of claim 11, wherein COV is selected from the group consisting of

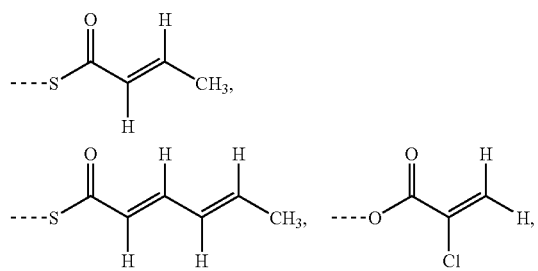

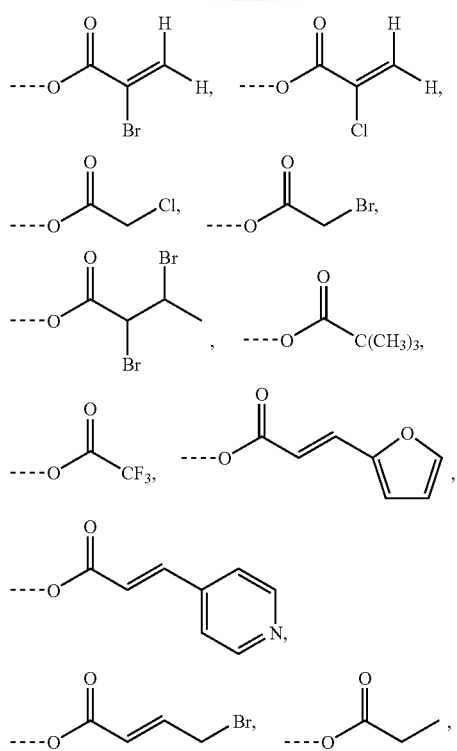

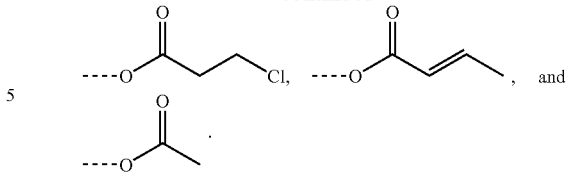

13. A pharmaceutical composition comprising a compound of claim 1 and a pharmaceutically acceptable carrier.

14. A method of inhibiting the growth of a cancer cell in a patient, the method comprising administering to said patient a pharmaceutical composition of claim 13 in an amount effective to inhibit cancer cell growth in the patient.

15. The method of claim 14, wherein the cancer cell is selected from the group consisting of breast, colon and colorectal, leukemia, pancreatic, central nervous system, non-small-cell lung, ovarian, prostate, melanoma, renal, fibrosarcoma, and urinary bladder cancer cells.

16. A method of inhibiting the growth of a cancer cell in vitro, the method comprising contacting the cancer cell with a compound of claim 1.

17. The method of claim 16, wherein 50% growth inhibition of said cancer cells is achieved with a concentration of said compound ($GI_{50}$) of less than about 50 micromolar.

18. A method for the treatment of cancer in a patient, the method comprising administering to said patient a pharmaceutical composition of claim 13 in an amount effective to treat cancer in the patient.

* * * * *